(12) United States Patent
Look et al.

(10) Patent No.: US 8,603,796 B2
(45) Date of Patent: Dec. 10, 2013

(54) METHOD FOR PRODUCING STORAGE STABLE VIRUSES AND IMMUNOGENIC COMPOSITIONS THEREOF

(75) Inventors: Jee Loon Look, Cary, NC (US); Vladimir G. Frolov, Gaithersburg, MD (US); Nandini Konar, Lancaster, PA (US)

(73) Assignee: Wyeth LLC, New York, NY (US)

( * ) Notice: Subject to any disclaimer, the term of this patent is extended or adjusted under 35 U.S.C. 154(b) by 1434 days.

(21) Appl. No.: 10/582,461

(22) PCT Filed: Dec. 10, 2004

(86) PCT No.: PCT/US2004/041803
§ 371 (c)(1),
(2), (4) Date: Feb. 26, 2008

(87) PCT Pub. No.: WO2005/058356
PCT Pub. Date: Jun. 30, 2005

(65) Prior Publication Data
US 2008/0206281 A1 Aug. 28, 2008

Related U.S. Application Data

(60) Provisional application No. 60/530,325, filed on Dec. 17, 2003.

(51) Int. Cl.
C12N 1/04 (2006.01)
C12N 7/00 (2006.01)
A61K 39/155 (2006.01)

(52) U.S. Cl.
USPC .................................... 435/235.1; 424/211.1

(58) Field of Classification Search
None
See application file for complete search history.

(56) References Cited

U.S. PATENT DOCUMENTS

| | | | |
|---|---|---|---|
| 4,084,330 A | 4/1978 | Fraser | |
| 4,273,762 A | 6/1981 | McAleer et al. | |
| 5,489,266 A | 2/1996 | Grimard | |
| 5,732,837 A | 3/1998 | Jones | |
| 5,882,651 A | 3/1999 | Murphy et al. | |
| 5,932,222 A | 8/1999 | Randolph et al. | |
| 5,993,824 A | 11/1999 | Murphy et al. | |
| 6,077,514 A | 6/2000 | Maassab et al. | |
| 6,284,254 B1 | 9/2001 | Murphy et al. | |
| 6,290,967 B1 * | 9/2001 | Volkin et al. | 424/204.1 |
| 6,410,023 B1 | 6/2002 | Durbin et al. | |

FOREIGN PATENT DOCUMENTS

| | | |
|---|---|---|
| WO | WO-99/62500 | 12/1999 |
| WO | WO-02/28422 | 4/2002 |
| WO | WO-03/086443 | 10/2003 |
| WO | WO-02/09749 | 3/2004 |
| WO | WO-2004/017990 | 3/2004 |

OTHER PUBLICATIONS

Heidemann et al. Cytotechnology 2000 vol. 32, pp. 157-167.*
Suzuki, M., J Hygiene (Lond). Mar. 1970; vol. 68(1): pp. 29-41.*
Buck et al. (1991) Chapter 2 and Chapter 6. In P.F. Simione and E.M. Brown (Ed.), ATCC Preservation Methods: Freezing and Freeze-Drying. p. i-iv and 1-42. Rockville, MD: ATCC.*
Gassier et al. (2004). Development of a new concept for bulk freeze-drying: Lyoguard freeze-dry packaging. In L. Ray and S.C. May (Ed.), Freeze-drying/lyophilization of pharmarceutical and biological products. p. 325-348. New York, NY: Marcel Dekker, Inc.*
Arya, "Stabilization of Vaccines: To Be or Not to Be", Vaccine, 19:595-597 (2001).
Carpenter et al., "5—Rational Design of Stable Lyophilized Protein Formulations: Theory and Practice", in *Rational Design of Stable Protein Formulations*, Klumer Academic/Plenum Publishers, New York, NY: 109-33 (2002).
Chanock et al., "Serious Respiratory Tract Disease Caused by Respiratory Syncytial Virus: Prospects for Improved Therapy and Effective Immunization" Pediatrics, 90:137-142 (Jul. 1, 1992).
Crowe et al., "Current Approaches to the Development of Vaccines Against Disease Caused by Respiratory Syncytial Virus (RSV) and Parainfluenza Virus (PIV): A Meeting Report fro the WHO Programme for Vaccine Development" Vaccine, 13:415-421 (Mar. 1995).
Franks et al., "Freeze-Drying: from Empiricism to Predictability. The Significance of Glass Transitions" Dev. Biol. Stand., 74:9-18 (1992).
Glezen et al., "Risk of Respiratory Syncytial Virus Infection for Infants from Low-Income Families in Relationship to Age, Sex, Ethnic Group, and Maternal Antibody Level", J. Pediatr. 98:708-715 (May 1981).
Gupta et al., "Restoration of Suppressor T-Cell Functions in Children with AIDS Following Intravenous Gamma Globulin Treatment", Am. J. Dis. Child, 140:143-146 (Feb. 1986).
Gupta et al., "Stabilization of RSV Against Thermal Inactivation and Freeze-Thaw Cycles for the Development and Control of RSV Vaccines and Immune Globulin" Vaccine, 14:1417-1420 (Oct. 1996).
Hambling et al., Survival of the RSV During Storage Under Various Conditions, Br. J. Exp. Pathol., 45:647-655 (Dec. 1964).
Hatley, "The Effective Use of Differential Scanning Calorimetry in the Optimsation of Freeze-Drying Processes and Formulations", Dev. Biol. Stand. 74:105-119 (1992).
Hilleman et al., "Improving the Heat Stability of Vaccines: Problems, Needs, and Approaches", Rev. Infect. Dis., 11(Suppl. 3): S613-616 (May-Jun. 1989).
Jackson et al., "Safety of a Trivalent Live Attenuated Intranasal Influenza Vaccine, FluMist™?, Administered in Addition to Parenteral Trivalent Inactivated Influenza Vaccine to Seniors with Chromic Medical Conditions", Vaccine, 17(15-16):1905-1909 (Apr. 9, 1999).

(Continued)

*Primary Examiner* — Mary E Mosher
*Assistant Examiner* — Nick Zou
(74) *Attorney, Agent, or Firm* — Austin W. Zhang

(57) ABSTRACT

The invention relates to methods for producing storage stable virus compositions. In certain embodiments, the invention relates to one or more formulations and process steps which result in storage stable virus compositions, wherein the composition is storage stable as a lyophilized solid composition or a frozen liquid composition.

18 Claims, 2 Drawing Sheets

(56) References Cited

OTHER PUBLICATIONS

Katz et al., "Appendix N: Prospects for Immunizing Against Respiratory Syncytial Virus", in *New Vaccine Development Establishing Priorities*, vol. 1, Washington, National Academic Press, pp. 397-409 (1985).

Kneyber et al., "Current Concepts on Active Immunization Against Respiratory Syncytial Virus for Infants and Young Children" Pediatr. Infect. Dis. J., 21(7):685-696 (Jul. 2002).

Labconco, "FreeZone 1 Liter Benchtop Freeze Dry Systems: User's Manual" [Online] from www.labconco.com/manual/freeze, p. 24 (2003).

Lemon et al., "The Thermostability of Vaccines", Int. J. Technol. Assess. Health Care, 10(1):177-184 (1994).

Makoschey et al., "Serum-Free Produced Bovine Herpesvirus Type 1 and Bovine Parainfluenza Type 3 Virus Vaccines are Efficacious and Safe", Cytotechnol., 39(3):139-145 (2002).

Martin et al., "Epidemiology of Respiratory Viral Infection Among Paediatric Inpatients Over a Six-year Period in North-East England", J. Lancet, 1035-1038 (Nov. 11, 1978).

McConnochie et al., "Variation in Severity of Respiratory Syncytial Virus Infections with Subtype", J. Pediatr., 117(1)(1):52-62 (Jul. 1990).

Melnick et al., "Effect of pH on Thermal Stabilization of Oral Poliovirus Vaccine by Magnesium Chloride", Proc. Soc. Exp. Biol. Med., 112:894-897 (Apr. 1963).

Phillips et al., "A Study of Water Binding in Lyophilized Viral Vaccine Systems", Cryobiology, 18(4):414-419 (Aug. 1981).

Rasmussen et al., "Inadequate Poliovirus Immunity Levels in Immunized Illinois Children", Am. J. Dis. Child, 126:465-469 (Oct. 1973).

Robbins et al., "Obstacles to Developing Vaccines for the Third World" Sc. Am., 259:126-133 (Nov. 1988).

Stark et al., "Occurrence of Respiratory Syncytial Virus Subtypes in Hospitalized Children in Cleveland, Ohio from 1985-1988", Pediatr. Pulmonol., 11:98-102 (1991).

Tannock et al., "Freeze-Drying of Respiratory Syncytial Viruses for Transportation and Storage", J. Clin. Microbiol., 25(9):1769-1771 (1987).
Wertz et al., "Approaches to Immunization Against Respiratory Syncytial Virus", Biotech., 20:151-176 (1992).
Wulff et al., "Respiratory Syncytial Virus: Properties of Strains Propagated in Monkey Kidneys Cell Cultures", Proc. Soc. Exp. Biol. Med., 115:458-462 (Feb. 1964).

* cited by examiner

METHOD FOR PRODUCING STORAGE STABLE VIRUSES AND IMMUNOGENIC COMPOSITIONS THEREOF

CROSS-REFERENCE TO RELATED APPLICATIONS

This application is a national stage of International Patent Application No. PCT/US2004/041803, filed Dec. 10, 2004, which claims the benefit of the priority of U.S. Provisional Patent Application No. 60/530,325, filed Dec. 17, 2003.

FIELD OF THE INVENTION

The present invention generally relates to the fields of virology, viral formulation and process development. More particularly, the invention relates to methods for producing storage stable virus compositions, wherein the compositions are storage stable as a lyophilized solid composition or a frozen liquid composition.

BACKGROUND OF THE INVENTION

Human respiratory syncytial virus (RSV) and parainfluenza virus (PIV), members of the paramyxovirus family, are major pathogens responsible for severe respiratory disease in infants and young children (Glezen et al., 1981; Chanock et al., 1992; Martin et al., 1978). Two groups of RSV, group A (RSV-A) and group B (RSV-B), circulate simultaneously during yearly winter epidemics, although a predominance of Group A infections is usually noted (McConnochie et al., 1990; Stark et al., 1991). PIV type 3 (PIV-3) is a common cause of bronchiolitis, pneumonia and croup. Together, RSV and PIV-3 account for up to 30% of all hospitalizations of infants and young children for respiratory tract disease (Crowe, 1995). PIV types 1 and 2 (PIV-1 and PIV-2) are also common causes of croup. RSV has also been reported to cause significant morbidity in immunocompromised individuals and the elderly. Sixty-five million RSV infections occur globally every year, resulting in 160,000 deaths (Robbins and Freeman, 1988). In the United States alone, 100,000 children are hospitalized annually with severe cases of pneumonia and bronchiolitis resulting from an RSV infection (Glezen et al., 1986; Katz, 1985). Inpatient and ambulatory care for children with RSV infections in the U.S. was estimated in 1992 to cost in excess of $340 million per year (Wertz and Sullender, 1992). The World Health Organization (WHO) (Crowe, 1995) and the National Institute of Allergy and Infectious Disease (NIAID) vaccine advisory committees have ranked RSV second only to HIV for vaccine development, while the preparation of an efficacious PIV (e.g., PIV type 3) vaccine is ranked in the top ten vaccines considered a priority for vaccine development.

Thus, an urgent need remains for the ability to engineer a safe and effective RSV and/or PIV vaccine that is able to prevent serious respiratory diseases in infants, young children, elderly and the immunocompromised. The use of live attenuated RSV and/or PIV to control respiratory disease is one of the more promising approaches. A number of live attenuated RSV strains have been developed and tested in RSV-seronegative children during the past twenty years. The most pursued approaches for live attenuation of RSV have been cold-passaged (cp) RSV, temperature-sensitive (ts) RSV mutants and cold-passage temperature sensitive (cpts) RSV mutants (Kneyber and Kimpen, 2002). RSV mutants such as cpts-248, cpts-248/404, cpts-530 and PIV-3 mutant cp-45 are currently being evaluated in laboratories and clinical trials.

In addition to a need for the identification and development of an efficacious live attenuated RSV, PIV or RSV/PIV combination immunogenic compositions, there is currently a need for methods of producing storage stable RSV and/or PIV compositions and immunogenic compositions thereof. For example, RSV is a heat labile virus, which is inactivated in less than three months during storage at −65° C. to −86° C. (Hambling, 1964; Wulff et al., 1964; Gupta et al., 1996). It is therefore highly desirable to identify methods for producing RSV, PIV or RSV/PIV immunogenic compositions which are storage stable.

Furthermore, enhancing the storage stability of other viral immunogenic compositions has long been recognized as an important goal for improving the impact of vaccines on world health (Melnick and Wallis, 1963; Rasmussen et al., 1973; Ayra, 2001; Hilleman, 1989; Lemon and Milstein, 1994). There is therefore a need in the art of virus formulation and process development for methods of producing storage stable virus compositions such as herpes simplex virus, cytomegalovirus, Epstein-Barr virus, Varicella-Zoster virus, mumps virus, measles virus, influenza virus, poliovirus, rhinovirus, adenovirus, hepatitis A virus, hepatitis B virus, hepatitis C virus, Norwalk virus, togavirus, alphavirus, rubella virus, rabies virus, Marburg virus, Ebola virus, papilloma virus, polyoma virus, metapneumovirus, coronavirus, vesicular stomatitis virus, Venezuelan equine encephalitis virus and the like.

SUMMARY OF THE INVENTION

The present invention broadly relates to processes for producing storage stable virus compositions and immunogenic compositions thereof. In certain embodiments, the invention is directed to processes for producing storage stable virus compositions comprising a respiratory syncytial virus (RSV), a parainfluenza virus (PIV), or a combination thereof. More particularly, in certain embodiments, the invention relates to one or more formulations and process steps which result in storage stable virus compositions, wherein the virus composition is storage stable as a lyophilized solid composition or a frozen liquid composition. In one particular embodiment, the invention relates to one or more formulations and process steps which result in storage stable RSV, PIV or RSV/PIV compositions, wherein the RSV, PIV or RSV/PIV composition is storage stable as a lyophilized solid composition or a frozen liquid composition.

Thus, in certain embodiments, the invention is directed to a process for producing a small volume storage stable virus composition. In one particular embodiment, the invention is directed to a process for producing a small volume storage stable virus composition comprising RSV, a PIV, or a combination thereof, the process comprising (a) freezing the virus composition below its glass transition temperature in a time of about sixty minutes or less and (b) lyophilizing the virus composition, wherein the lyophilized virus composition is stable for at least one year at a storage temperature of about 1° C. to about 10° C. In one embodiment, the glass transition temperature is a temperature of about −45° C. and is reached in a time of about sixty minutes or less. In another embodiment, the glass transition temperature is a temperature of about −35° C. and is reached in a time of about forty minutes or less. In still another embodiment, the glass transition temperature of about −35° C. is reached in a time of about twenty minutes or less. In one embodiment, the volume of the virus composition is about 0.2 mL to about 1.0 mL. In certain embodiments, the virus composition is comprised in a suitable container means, wherein the container means is further defined as a vial, a tube or a nasal spray device. In one embodiment, the RSV is further defined as group A RSV (RSV-A), group B RSV (RSV-B), or a chimeric recombinant RSV comprising one or more antigens of each of group A and B (RSV-AB), and the PIV is further defined as PIV type 1 (PIV-1), PIV type 2 (PIV-2) or PIV type 3 (PIV-3).

In certain embodiments, a small volume storage stable virus composition is formulated in a 5.0 mM to about 20 mM phosphate buffer solution comprising sodium and/or potassium monobasic and dibasic salts and having a pH of about 6.5 to about 7.8. In other embodiments, the 5.0 mM to about 20 mM phosphate buffer solution further comprises about 0.25 mM to about 25 mM N-2-hydroxyethylpiperazine-N'-2-ethanesulfonic acid (HEPES). In certain other embodiments, the 5.0 mM to about 20 mM phosphate buffer solution further comprises about 0.01 mM to about 1 mM magnesium chloride and about 0.01 mM to about 1 mM calcium chloride.

In certain embodiments, a small volume storage stable virus composition is formulated in a 10 mM phosphate buffer solution comprising sodium and/or potassium monobasic and dibasic salts and having a pH of about 6.5 to about 7.8. In other embodiments, the 10 mM phosphate buffer solution further comprises about 0.25 mM to about 25 mM HEPES. In certain other embodiments, the 10 mM phosphate buffer solution further comprises about 0.01 mM to about 1 mM magnesium chloride and about 0.01 mM to about 1 mM calcium chloride.

In one embodiment, the 5.0 mM to about 20 mM phosphate buffer solution (pH of about 6.5 to about 7.8) comprising about 0.25 mM to about 25 mM HEPES, about 0.01 mM to about 1 mM magnesium chloride and about 0.01 mM to about 1 mM calcium chloride, further comprises sucrose, L(+)-glutamic acid, L(+)-glutamic acid monosodium salt, a mixture of L(+)-glutamic acid and L(+)-glutamic acid monosodium salt, human albumin (HA) and/or soy peptone. In other embodiments, the 5.0 mM to about 20 mM phosphate buffer solution, with a pH of about 6.5 to about 7.8, comprising about 0.25 mM to about 25 mM HEPES, about 0.01 mM to about 1 mM magnesium chloride, and about 0.01 mM to about 1 mM calcium chloride, further comprises about 50 g/L sucrose, about 0.049 mM to about 4.9 mM L(+)-glutamic acid or about 0.049 mM to about 4.9 mM L(+)-glutamic acid monosodium salt or a mixture thereof, and about 1.0 g/L to about 10.0 g/L HA. In another embodiment, the about 1.0 g/L to about 10.0 g/L HA is substituted with about 50 g/L soy peptone. In still other embodiments, the 5.0 mM to about 20 mM phosphate buffer solution, with a pH of about 6.5 to about 7.8, comprises about 0.25 mM to about 25 mM HEPES, about 0.01 mM to about 1 mM magnesium chloride, about 0.01 mM to about 1 mM calcium chloride, about 50 g/L sucrose, about 0.049 mM to about 4.9 mM L(+)-glutamic acid or about 0.049 mM to about 4.9 mM L(+)-glutamic acid monosodium salt or a mixture thereof, about 1.0 g/L to about 10.0 g/L HA and about 50 g/L soy peptone.

In one embodiment, the 10 mM phosphate buffer solution, with a pH of about 6.5 to about 7.8, comprising about 0.25 mM to about 12.5 mM HEPES, about 0.01 mM to about 0.5 mM magnesium chloride and about 0.01 mM to about 0.5 mM calcium chloride, further comprises about 50 g/L sucrose, about 0.049 mM to about 4.9 mM L(+)-glutamic acid or about 0.049 mM to about 4.9 mM L(+)-glutamic acid monosodium salt or a mixture thereof, and about 1.0 g/L to about 10.0 g/L HA. In other embodiments, the about 1.0 g/L to about 10.0 g/L HA is substituted with about 50 g/L soy peptone. In yet other embodiments, the 10 mM phosphate buffer solution, with a pH of about 6.5 to about 7.8, comprises about 0.25 mM to about 12.5 mM HEPES, about 0.01 mM to about 0.5 mM magnesium chloride, about 0.01 mM to about 0.5 mM calcium chloride, about 50 g/L sucrose, about 0.049 mM to about 2.45 mM L(+)-glutamic acid or about 0.049 mM to about 2.45 mM L(+)-glutamic acid monosodium salt or a mixture thereof, about 1.0 g/L to about 10.0 g/L HA and about 50 g/L soy peptone.

In one embodiment, the storage temperature of the small volume storage stable virus composition is about 5° C. In certain other embodiments, the virus composition has less than about a 1.0 log PFU loss after one year of storage at about 1° C. to about 10° C. In yet another embodiment, the virus composition is at least 4.0 log PFU per 0.2 mL after one year of storage at about 1° C. to about 10° C.

In one embodiment, lyophilizing the virus composition is further defined as (a) placing about 0.5 mL to 0.6 mL of the virus composition in a vial and cooling to a temperature of about 5° C.; (b) placing the vial on a lyophilization shelf and decreasing the shelf temperature from 5° C. to −50° C. at a rate of about −1.0° C. per minute to about −2.0° C. per minute; (c) holding the shelf temperature at about −50° C. for 60 minutes; (d) reducing the lyophilization chamber pressure to 0.10 Torr and holding the shelf temperature at about −50° C. for 30-60 minutes; (e) increasing the shelf temperature from −50° C. to 0° C. at a rate of about 1.0° C. per minute to about 2.0° C. at about 0.10 Torr and holding the shelf temperature at about 0° C. for about 540 minutes to about 720 minutes; (f) increasing the shelf temperature from 0° C. to 15° C. at a rate of about 0.5° C. per minute at about 0.10 Torr and holding the shelf temperature at about 15° C. for about 600 minutes to about 720 minutes and (g) filling the vial with nitrogen gas and hermetically sealing the vial.

In another embodiment, lyophilizing the virus composition is further defined as (a) placing about 0.5 mL to 0.6 mL of the virus composition in a vial and cooling to a temperature of about 5° C.; (b) freezing a lyophilization shelf to a temperature of about −70° C.; (c) placing the vial on the lyophilization shelf and holding the temperature at about −70° C. for about 60 minutes; (d) reducing the lyophilization chamber pressure to 0.10 Torr and increasing the shelf temperature from −70° C. to −50° C. at a rate of about 1.0° C. per minute; (e) increasing the shelf temperature from −50° C. to 0° C. at a rate of about 1.0° C. per minute to about 2.0° C. per minute at about 0.10 Torr and holding the shelf temperature at about 0° C. for about 540 minutes to about 720 minutes; (f) increasing the shelf temperature from 0° C. to 15° C. at a rate of about 0.5° C. per minute at about 0.10 Torr and holding the shelf temperature at about 15° C. for about 600 minutes to about 720 minutes and (g) filling the vial with nitrogen gas and hermetically sealing the vial.

In yet another embodiment, the invention is directed to a process for producing a bulk (or large) volume, lyophilization stable virus composition. In one particular embodiment, the invention is directed to a process for producing a bulk (or large) volume, lyophilization stable virus composition comprising RSV, PIV, or a combination thereof, the process comprising (a) placing a liquid virus composition having a volume of at least 50 mL in a lyophilization tray; (b) freezing the virus composition in a liquid nitrogen bath for at least twenty minutes and (c) lyophilizing the virus composition, wherein the lyophilized virus composition has less than about a 0.5 log PFU loss relative to the virus composition before lyophilization. In still other embodiments, the bulk volume virus composition is at least 5.0 log PFU per dose after lyophilization. In one embodiment, the glass transition temperature is a temperature of about −35° C. In another embodiment, the glass transition temperature is a temperature of about −30° C. to about −40° C. In still another embodiment, the lyophilization tray is a Lyoguard® lyophilization tray (W. L. Gore and Associates; Newark, Del.). In one embodiment, the bulk volume of the virus composition is at least 500 mL per lyophilization tray. In other embodiments, the bulk volume of the virus composition is at least 1000 mL per lyophilization tray. In one embodiment, the RSV is further defined as RSV-A, RSV-B, or a chimeric recombinant RSV comprising one or more antigens of each of group A and B (RSV-AB), and the PIV is further defined as PIV-1, PIV-2 or PIV-3.

In one embodiment, the bulk volume virus composition is formulated in a 5.0 mM to about 20 mM phosphate buffer solution comprising sodium and/or potassium monobasic and dibasic salts and having a pH of about 6.5 to about 7.8. In other embodiments, the 5.0 mM to about 20 mM phosphate buffer solution further comprises about 2.5 mM to about 25 mM HEPES. In certain other embodiments, the 5.0 mM to about 20 mM phosphate buffer solution further comprises about 0.1 mM to about 1 mM magnesium chloride and about 0.1 mM to about 1 mM calcium chloride.

In certain embodiments, the bulk volume virus composition is formulated in a 10 mM phosphate buffer solution comprising sodium and/or potassium monobasic and dibasic salts and having a pH of about 6.5 to about 7.8. In other embodiments, the 10 mM phosphate buffer solution further comprises about 2.5 mM to about 25 mM HEPES. In certain other embodiments, the 10 mM phosphate buffer solution further comprises about 0.1 mM to about 1 mM magnesium chloride and about 0.1 mM to about 1 mM calcium chloride.

In one embodiment, the 5.0 mM to about 20 mM phosphate buffer solution, with a pH of about 6.5 to about 7.8, comprising about 2.5 mM to about 25 mM HEPES, about 0.1 mM to about 1 mM magnesium chloride and about 0.1 mM to about 1 mM calcium chloride, further comprises sucrose, L(+)-glutamic acid, L(+)-glutamic acid monosodium salt, a mixture of L(+)-glutamic acid and L(+)-glutamic acid monosodium salt, human albumin (HA) and/or soy peptone. In other embodiments, the 5.0 mM to about 20 mM phosphate buffer solution, with a pH of about 6.5 to about 7.8, comprising about 2.5 mM to about 25 mM HEPES, about 0.1 mM to about 1 mM magnesium chloride and about 0.1 mM to about 1 mM calcium chloride, further comprises about 50 g/L sucrose, about 0.049 mM to about 4.9 mM L(+)-glutamic acid or about 0.049 mM to about 4.9 mM L(+)-glutamic acid monosodium salt or a mixture thereof, and about 1.0 g/L to about 10.0 g/L HA. In one embodiment, the about 1.0 g/L to about 10.0 g/L HA is substituted with about 50 g/L soy peptone. In other embodiments, the 5.0 mM to about 20 mM phosphate buffer solution, with a pH of about 6.5 to about 7.8, comprises about 2.5 mM to about 25 mM HEPES, about 0.1 mM to about 1 mM magnesium chloride, about 0.1 mM to about 1 mM calcium chloride, about 50 g/L sucrose, about 0.049 mM to about 4.9 mM L(+)-glutamic acid or about 0.049 mM to about 4.9 mM L(+)-glutamic acid monosodium salt or a mixture thereof, about 1.0 g/L to about 10.0 g/L HA and about 50 g/L soy peptone.

In still other embodiments, the 10 mM phosphate buffer solution, with a pH of about 6.5 to about 7.8, comprising about 2.5 mM to about 12.5 mM HEPES, about 0.1 mM to about 0.5 mM magnesium chloride and about 0.1 mM to about 0.5 mM calcium chloride, further comprises about 50 g/L sucrose, about 0.049 mM to 2.45 mM L(+)-glutamic acid or about 0.049 mM to about 2.45 mM L(+)-glutamic acid monosodium salt or a mixture thereof, and about 1.0 g/L to about 10.0 g/L HA. In yet other embodiments, the about 1.0 g/L to about 10.0 g/L HA is substituted with about 50 g/L soy peptone. In yet another embodiments, the 10 mM phosphate buffer solution, with a pH of about 6.5 to about 7.8, comprises about 2.5 mM to about 12.5 mM HEPES, about 0.1 mM to about 0.5 mM magnesium chloride, about 0.1 mM to about 0.5 mM calcium chloride, about 50 g/L sucrose, about 0.049 mM to 2.45 mM L(+)-glutamic acid or about 0.049 mM to about 2.45 mM L(+)-glutamic acid monosodium salt or a mixture thereof, about 1.0 g/L to about 10.0 g/L HA and about 50 g/L soy peptone.

In certain other embodiments, lyophilizing the bulk volume virus composition is further defined as (a) placing the lyophilization tray comprising the frozen virus composition at a temperature of about −50° C. on a lyophilization shelf pre-cooled to a temperature of about −50° C. and holding the temperature for about 60 minutes; (b) reducing chamber pressure to 0.10 Torr and increasing the shelf temperature from −50° C. to −23° C. at a rate of about 0.23° C. per minute at about 0.10 Torr; (c) holding the shelf temperature at about −23° C. for about 80 hours to about 100 hours; (d) reducing the lyophilization chamber pressure to 0.02 Torr and increasing the shelf temperature from −23° C. to 15° C. at a rate of about 0.23° C. per minute; (e) holding the shelf temperature at about 15° C. and at about 0.02 Torr for about 30 hours to about 40 hours; (f) increasing the shelf temperature from 15° C. to 25° C. at a rate of about 0.17° C. per minute at 0.02 Torr; (g) holding the shelf temperature at about 25° C. and at about 0.02 Torr for about 10 hours and (h) filling the chamber with nitrogen gas and hermetically sealing the tray under nitrogen gas in an aluminum pouch.

In other embodiments, lyophilizing the bulk volume virus composition is further defined as (a) placing the tray comprising the frozen virus composition at a temperature of about −70° C. on a lyophilization shelf pre-cooled to a temperature of about −70° C. and holding the temperature for about 60 minutes; (b) reducing chamber pressure to 0.10 Torr and increasing the shelf temperature from −70° C. to −23° C. at a rate of about 0.23° C. per minute; (c) holding the shelf temperature at about −23° C. at about 0.10 Torr for about 80 to 100 hours; (d) reducing chamber pressure to 0.02 Torr and increasing the shelf temperature from −23° C. to 15° C. at a rate of about 0.23° C. per minute; (e) holding the temperature at about 15° C. and 0.02 Torr for about 30 to 40 hours; (f) increasing the shelf temperature from 15° C. to 25° C. at a rate of about 0.17° C. per minute at 0.020 Torr; (g) holding the temperature at about 25° C. for about 10 hours and (h) filling the chamber with nitrogen gas and hermetically sealing the tray under nitrogen gas in an aluminum pouch.

In other embodiments, the invention is directed to a process for producing a storage stable frozen liquid virus composition. In one particular embodiment, the invention is directed to a process for producing a storage stable frozen liquid virus composition comprising RSV, PIV, or a combination thereof, the process comprising (a) equilibrating a metal plate in a liquid nitrogen bath; (b) placing a liquid virus composition in a suitable container means; (c) inserting the container of step (b) into a metal holder; (d) placing the metal holder on the equilibrated metal plate of step (a) for about ten minutes; (e) removing the container from the metal holder and (f) storing the container at temperature from about −20° C. to about −70° C., wherein the virus composition after steps (a) through (f) has less than about a 0.5 log PFU loss after 6 months storage. In certain embodiments, the container means is a nasal spray device. In one embodiment, the nasal spray device is a BD Accuspray™ nasal spray device (BD Medical Pharmaceutical Systems; Franklin Lakes, N.J.). In another embodiment, the metal holder is aluminum. In still another embodiment, the metal holder is stainless steel. In other embodiments, the virus composition is at least 4.0 log PFU/0.2 mL after steps (a) through (f). In yet another embodiment, the virus composition is at least 4.0 log PFU/0.2 mL after a six month storage at a temperature of −20° C. In other embodiments, the virus composition is at least 4.0 log PFU/0.2 mL after a six month storage at a temperature of −70° C. In certain embodiments, the liquid virus composition is formulated in the absence of a protein stabilizer. In one embodiment, the RSV is further defined as RSV-A, RSV-B, or a chimeric recombinant RSV comprising one or more antigens of each of group A and B (RSV-AB), and the PIV is further defined as PIV-1, PIV-2 or PIV-3.

In certain other embodiments, the liquid virus composition is formulated in a 5.0 mM to about 20 mM phosphate buffer solution comprising sodium and/or potassium monobasic and dibasic salts and having a pH of about 6.5 to about 7.8. In other embodiments, the 5.0 mM to about 20 mM phosphate buffer solution further comprises about 0.25 mM to about 25 mM HEPES. In certain other embodiments, the 5.0 mM to about 20 mM phosphate buffer solution further comprises about 0.01 mM to about 1 mM magnesium chloride and about 0.01 mM to about 1 mM calcium chloride.

In certain embodiments, the liquid virus composition is formulated in a 10 mM phosphate buffer solution comprising sodium and/or potassium monobasic and dibasic salts and having a pH of about 6.5 to about 7.8. In other embodiments, the mM phosphate buffer solution further comprises about 0.25 mM to about 25 mM HEPES. In certain other embodiments, the 10 mM phosphate buffer solution further comprises about 0.01 mM to about 1 mM magnesium chloride and about 0.01 mM to about 1 mM calcium chloride.

In one embodiment, the 5.0 mM to about 20 mM phosphate buffer solution, with a pH of about 6.5 to about 7.8, comprising about 0.25 mM to about 25 mM HEPES, about 0.01 mM to about 1 mM magnesium chloride and about 0.01 mM to about 1 mM calcium chloride, further comprises sucrose and L(+)-glutamic acid, L(+)-glutamic acid monosodium salt or a mixture thereof. In other embodiments, the 5.0 mM to about 20 mM phosphate buffer solution, with a pH of about 6.5 to about 7.8, comprising about 0.25 mM to about 25 mM HEPES, about 0.01 mM to about 1 mM magnesium chloride and about 0.01 mM to about 1 mM calcium chloride, further comprises about 75 g/L sucrose and about 4.9 mM L(+)-glutamic acid or about 4.9 mM L(+)-glutamic acid monosodium salt or about a 4.9 mM mixture of L(+)-glutamic acid and L(+)-glutamic acid monosodium salt.

In still other embodiments, the 10 mM phosphate buffer solution, with a pH of about 6.5 to about 7.8, comprising about 0.25 mM to about 25 mM HEPES, about 0.01 mM to about 1 mM magnesium chloride and about 0.01 mM to about 1 mM calcium chloride, further comprises about 75 g/L sucrose and about 4.9 mM L(+)-glutamic acid or about 4.9 mM L(+)-glutamic acid monosodium salt or about a 4.9 mM mixture of L(+)-glutamic acid and L(+)-glutamic acid monosodium salt.

In another embodiment, the invention is directed to a small volume lyophilized virus composition produced according to the process of freezing a virus composition below its glass transition temperature in a time of sixty minutes or less and lyophilizing the virus composition, wherein the lyophilized virus composition is a stable for at least one year at a storage temperature of about 1° C. to about 10° C.

In yet another embodiment, the invention is directed to a bulk volume lyophilized virus composition produced according to the process of placing a liquid virus composition having a volume of at least 50 mL in a lyophilization tray; freezing the virus composition below its glass transition temperature for at least about twenty minutes in a liquid nitrogen bath and lyophilizing the virus composition, wherein the lyophilized virus composition has less than about a 0.5 log PFU loss relative to the virus composition before lyophilization.

In still another embodiment, the invention is directed to a storage stable frozen liquid virus composition produced according to the process of (a) equilibrating a metal plate in a liquid nitrogen bath; (b) placing a liquid virus composition in a suitable container means; (c) inserting the container of step (b) into a metal holder; (d) placing the metal holder on the equilibrated metal plate of step (a) for about ten minutes; (e) removing the container from the metal holder and (f) storing the container at temperature from about −20° C. to about −70° C., wherein the virus composition after steps (a) through (f) has less than about a 0.5 log PFU loss after 6 months storage.

In certain other embodiments, the invention is directed to an immunogenic composition comprising a virus composition produced according to a lyophilization process of the invention, wherein the virus is dissolved, diluted or suspended in a pharmaceutically acceptable carrier.

In other embodiments, the invention is directed to an immunogenic composition comprising a frozen liquid virus composition produced according to a process of the invention.

Other features and advantages of the invention will be apparent from the following detailed description, from the preferred embodiments thereof, and from the claims.

DETAILED DESCRIPTION OF THE INVENTION

Figure 1:
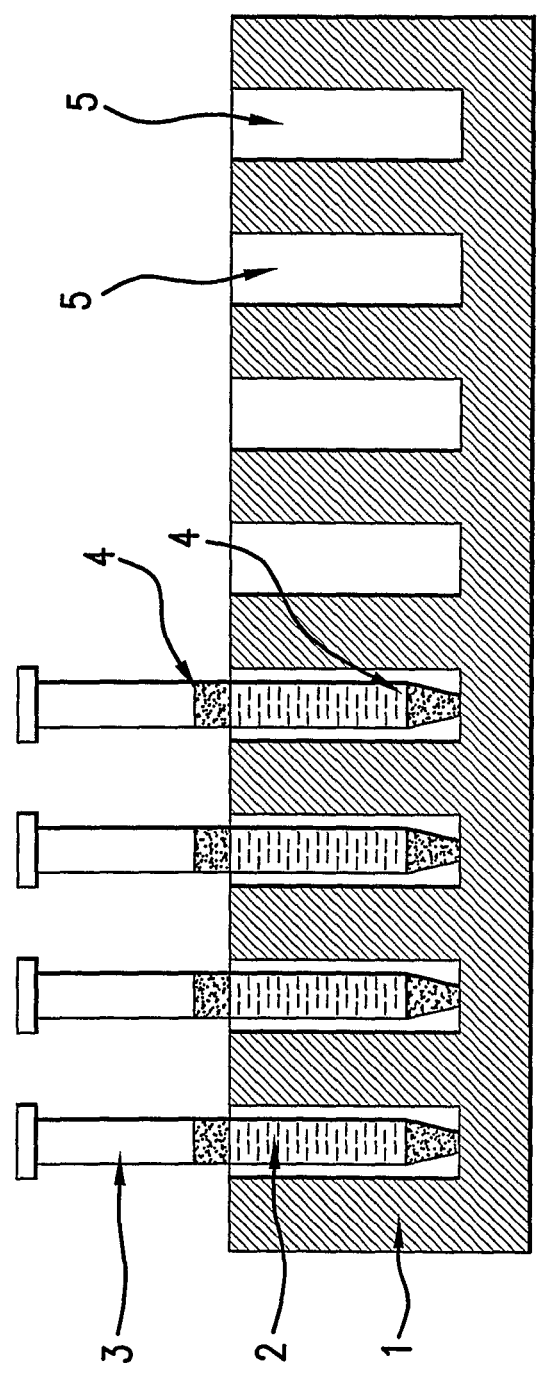
FIG. 1 shows a schematic representation of the positioning of the BD Accuspray™ devices in the 96 well aluminum holder that was used to freeze formulations, which is labeled as follows: (1) an aluminum or steel holder, (2) formulation filled into the device, (3) BD Accuspray device, (4) stoppers and (5) empty wells.

The invention described hereinafter, addresses a need in the art for methods of producing storage stable virus compositions. In certain embodiments, invention described hereinafter, addresses a need in the art for methods of producing storage stable virus compositions comprising respiratory syncytial virus (RSV), a parainfluenza virus (PIV), or a combination thereof, for use in immunogenic compositions which prevent or ameliorate respiratory disease in infants, young children, the elderly and immunocompromised.

In certain other embodiments, the invention addresses a need in the art for methods of producing storage stable virus compositions comprising one or more viruses such as herpes simplex virus, cytomegalovirus, Epstein-Barr virus, Varicella-Zoster virus, mumps virus, measles virus, influenza virus, poliovirus, rhinovirus, adenovirus, hepatitis A virus, hepatitis B virus, hepatitis C virus, Norwalk virus, togavirus, alphavirus, rubella virus, rabies virus, Marburg virus, Ebola virus, papilloma virus, polyoma virus, metapneumovirus, coronavirus, vesicular stomatitis virus, Venezuelan equine encephalitis virus and the like, for use in immunogenic compositions which prevent or ameliorate disease caused by one or more of these viruses.

Thus, in certain embodiments, the invention is directed to methods for producing small volumes of lyophilized virus compositions. In one particular embodiment, the invention is directed to methods for producing small volumes of lyophilized virus compositions, wherein the lyophilized composition is storage stable for at least one year at a storage temperature of about 1° C. to about 10° C. In certain other embodiments, the invention is directed to methods for producing large (or bulk) volumes of lyophilized virus compositions. In particular embodiments, the invention is directed to methods for producing large (or bulk) volumes of lyophilized virus compositions, wherein the lyophilized composition has less than about a 0.5 log plaque-forming units (PFU) loss relative to the composition before lyophilization. In another embodiment, the invention is directed to methods for producing frozen liquid virus compositions. In certain embodiments, the invention is directed to methods for producing frozen liquid virus compositions, wherein the composition has less than about a 0.5 log PFU loss after six months storage. In other embodiments, the invention provides storage stable virus compositions produced according to the methods of the invention. In other embodiments, the invention provides immunogenic compositions produced according to the methods of the invention.

A. VIRUS COMPOSITIONS

RSV belongs to the genus *Pneumoviridae*, which is classified within the family of Paramyxoviridae. The virion contains a single stranded negative sense RNA of 15,222 base pairs which codes for ten viral proteins. These ten proteins comprise three envelope-associated glycoproteins termed G, F and SH; two matrix proteins M and M2, three nucleocapsid proteins L, N and P and the nonstructural proteins 1B and 1C.

Two groups of RSV, group A and group B, are identified on the basis of antigenic differences in the G protein and to a lesser extent the F protein. Antigenic differences can be found within the two groups. The G protein shows a high degree of variation with only 53% amino acid homology between RSV groups A and B and up to 20% differences in G protein sequences within RSV group A. Hereinafter, "RSV group A" is represented as "RSV-A" and "RSV group B" is represented as "RSV-B".

A storage stable RSV composition (or RSV/PIV combination) produced according to one of the methods of the invention is any attenuated RSV (e.g., attenuated RSV-A and attenuated RSV-B) which includes, but is not limited to, cold-passaged RSV mutants (cpRSV), temperature-sensitive RSV mutants (tsRSV), cold-passaged temperature-sensitive RSV mutants (cptsRSV), cold-adapted RSV mutants (caRSV), small-plaque RSV mutants (spRSV), and the like. For example, U.S. Pat. Nos. 5,882,651, 5,932,222, 5,993,824, 6,077,514 and 6,284,254, each of which is incorporated herein by reference in its entirety, describe methods for producing various attenuated RSV phenotypes. In a preferred embodiment, an attenuated RSV of the invention is cptsRSV 248/404 (ATCC VR2452), also known as LRSV-404 and all recombinant modifications made from this strain including recombinant RSV-AB strains. Other exemplary RSV strains of the invention include: (a) rA2 cp248/404ΔSH (also known as LRSV-rA36); (b) rA2 cp248/404/1030ΔSH (also known as LRSV-rA38); (c) rA2 cp248/404/1030 (also known as LRSV-rA39); (d) rA2 cp248/404ΔNS2 (also known as LRSV-rA41); (e) rABcp248/404/1030 (also known as LRSV-rAB1); (f) rABcp248/404ΔSH (also known as LRSV-rAB2); (g) rABcp248/404ΔNS2 (also known as LRSV-rAB4); (h) cptsRSV 530/1009 (ATCC VR2451) and all recombinant modifications made from this strain including recombinant RSV-AB strains such as rA2 cp530/1009ΔNS2 (also known as LRSV-rA42); rA2 cp530/1009/404 (also known as LRSV-rA43); rABcp530/1009ΔNS2 (also known as LRSV-rAB3) and rABcp530/1009/404 (also known as LRSV-rAB6).

Human parainfluenza virus type 3 (PIV-3) is a member of the recently named Respirovirus genus of the Paramyxoviridae family. Its genome is a single strand of negative-sense RNA 15,462 nucleotides in length. At least eight proteins are encoded by PIV-3: the nucleocapsid protein NP, the phosphoprotein P, the nonstructural protein C, the D protein, the matrix protein M, the fusion glycoprotein F, the hemagglutinin-neuraminidase protein HN, and the large polymerase protein L. The HN and F proteins are envelope-associated, surface glycoproteins, which are the major neutralization and protective antigens. The significant sequence divergence between comparable PIV HN or F proteins among the PIV types (e.g., type 1, 2 and 3) is thought to be the basis for the type specificity of the protective immunity.

Human parainfluenza virus type 1 (PIV-1) is another member of the Respirovirus genus of the Paramyxoviridae. Its genome is a single strand of negative-sense RNA approximately 15,600 nucleotides in length. The order of gene products encoded by PIV-1 includes the nucleocapsid protein NP, the phosphoprotein P (and numerous other gene products encoded by the P open reading frame), the matrix protein M, the fusion glycoprotein F, the hemagglutinin-neuraminidase protein HN, and the large polymerase protein L.

Human parainfluenza virus type 2 (PIV-2) is a member of the Rubulavirus genus of the Paramyxoviridae. Its genome is a single strand of negative-sense RNA approximately 15,654 nucleotides in length. The order of gene products encoded by PIV-2 includes the nucleocapsid protein NP, the phosphoprotein P, the V protein, the matrix protein M, the fusion glycoprotein F, the hemagglutinin-neuraminidase protein HN, and the large polymerase protein L.

A storage stable PIV composition (or RSV/PIV combination) produced according to one of the methods of the invention is any attenuated PIV, which includes, but is not limited to, cold-passaged PIV mutants (cpPIV), temperature-sensitive PIV mutants (tsPIV), cold-passaged temperature-sensitive PIV mutants (cptsPIV), cold-adapted PIV mutants (caPIV), small-plaque PIV mutants (spPIV) and the like. In a preferred embodiment, an attenuated PIV of the invention is the cold-passaged PIV-3 mutant of the JS wild-type strain designated cp-45 (or JS cp45). In other preferred embodiments, the PIV-3 cp-45 mutant is further attenuated using the "menu" of attenuating PIV-3 mutations described in U.S. Pat. Nos. 6,410,023 and 5,869,036 (each incorporated herein by reference).

In other embodiments, a storage stable virus composition produced according to one of the methods of the invention includes, but is not limited to, one or more of the viruses, or vectors thereof, set forth in Table 1.

TABLE 1

| VIRUS FAMILIES |
|---|
| I. Picornaviridae |
| Enteroviruses |
| Poliovirus |
| Coxsackievirus |
| Echovirus |
| Rhinoviruses |
| Hepatitis A Virus |

TABLE 1-continued

VIRUS FAMILIES

II. Caliciviridae

Norwalk group of viruses
III. Togaviridae and Flaviviridae

Togaviruses (e.g., Dengue virus)
Alphaviruses
Flaviviruses (e.g., Hepatitis C virus)
Rubella virus
IV. Coronaviridae Coronaviruses
V. Rhabdoviridae Rabies virus
VI. Filoviridae Marburg viruses
Ebola viruses
VII. Paramyxoviridae Parainfluenza virus
Mumps virus
Measles virus
Respiratory syncytial virus
Metapneumovirus
VIII. Orthomyxoviridae Orthomyxoviruses (e.g., Influenza virus)
IX. Bunyaviridae Bunyaviruses
X. Arenaviridae Arenaviruses
XI. Reoviridae Reoviruses
Rotaviruses
Orbiviruses
XII. Retroviridae Human T Cell Leukemia Virus type I
Human T Cell Leukemia Virus type II
Human Immunodeficiency Viruses (e.g., type I and type II
Simian Immunodeficiency Virus
Lentiviruses
XIII. Papoviridae Polyomaviruses
Papillomaviruses
XIV. Parvoviridae Parvoviruses
XV. Herpesviridae Herpes Simplex Viruses
Epstein-Barr virus
Cytomegalovirus
Varicella-Zoster virus
Human Herpesvirus-6
human herpesvirus-7
Cercopithecine Herpes Virus 1 (B virus)
XVI. Poxviridae Poxviruses
XVIII. Hepadnaviridae Hepatitis B virus
XIX. Adenoviridae

B. SMALL VOLUMES OF STORAGE STABLE VIRUS

In certain embodiments, the invention is directed to a process for producing small volumes of storage stable virus compositions. In one embodiment, the invention is directed to a process for producing small volumes of storage stable virus compositions comprising RSV, PIV, or a combination thereof. The process comprises freezing the virus composition below its glass transition temperature ($T_g$) in a time of sixty minutes or less and lyophilizing the virus composition. The lyophilized virus composition, which is a solid powder or cake, is stable for at least one year at a storage temperature of about 1° C. to about 10° C. Small volumes of storage stable lyophilized virus compositions are of particular utility as single or multi-dosage immunogenic compositions, wherein the lyophilized powder is stored for a given amount of time.

A "small volume" of a virus composition is between about 100 μL to about 5 mL. In certain embodiments, a small volume virus composition is between about 200 μL to about 1 mL. In one embodiment, the volume of a virus composition is 500 μL.

Thus in certain embodiments, a small volume virus composition is frozen and lyophilized in a suitable container means. Typically, a suitable container means, with respect to small volume virus compositions, is a container which can withstand the freezing and lyophilization temperatures and vacuum pressures. For example, a suitable container means for the production of small volume storage stable compositions is a vial, a tube, a syringe, a two-stage syringe or a nasal spray device. See for example U.S. Pat. Nos. 5,489,266, 5,732,837 and 4,084,330, each of which is hereby incorporated by reference in its entirety. Additional container means for lyophilization are known and readily available to one of skill in the art.

1. SMALL VOLUME VIRUS FORMULATION

As defined hereinafter, a "RSV composition", a "PIV composition" or a "RSV/PIV composition" comprises the virus (i.e., RSV, PIV or RSV/PIV), typically about $10^3$ to $10^7$ PFU of attenuated virus per mL and a pharmaceutically acceptable carrier. A pharmaceutically acceptable carrier includes buffers, saline solutions, water, water for injection (WFI), protein stabilizers, sugars, amino acids, cryoprotectants, and the like.

A small volume virus composition is formulated in a 5.0 mM to about 20 mM phosphate buffer solution comprising sodium and/or potassium monobasic and dibasic salts and having a pH of about 6.5 to about 7.8. In certain formulations, the 5.0 mM to about 20 mM phosphate buffer solution further comprises about 0.25 mM to about 25 mM HEPES, about 0.01 mM to about 1 mM magnesium chloride and about 0.01 mM to about 1 mM calcium chloride.

In certain formulations, a small volume virus composition formulated in a 5.0 mM to about 20 mM phosphate buffer (pH of about 6.5 to about 7.8) comprising about 0.25 mM to about 25 mM HEPES, about 0.01 mM to about 1 mM magnesium chloride, about 0.01 mM to about 1 mM calcium chloride, further comprises sucrose, L(+)-glutamic acid, L(+)-glutamic acid monosodium salt or a mixture thereof, human alin (HA) and/or soy peptone. In certain other formulations, the 10 mM phosphate buffer solution (pH of about 6.5 to about 7.8) comprising about 0.25 mM to about 12.5 mM HEPES, about 0.01 mM to about 0.5 mM magnesium chloride and about 0.01 mM to about 0.5 mM calcium chloride, further comprises about 0.049 mM to about 2.45 mM L(+)-glutamic acid or about 0.049 mM to about 2.45 mM L(+)-glutamic acid monosodium salt or a mixture thereof, about 50 g/L sucrose and about 1.0 g/L to about 10.0 g/L HA. In other certain formulations, the about 1.0 g/L to 10.0 g/L HA is substituted with about 50 g/L soy peptone (also known as Hy-Soy®; Quest International; Chicago, Ill.). In another formulation, the stable small volume virus compositions is formulated in the 5.0 mM to about 20 mM phosphate buffer solution (pH of about 6.5 to about 7.8) comprising about 0.25 mM to about 25 mM HEPES, about 0.01 mM to about 1 mM magnesium chloride, about 0.01 mM to about 1 mM calcium chloride, about 50 g/L sucrose, about 0.049 mM to about 4.9 mM L(+)-glutamic acid or about 0.049 mM to about 4.9 mM L(+)-glutamic acid monosodium salt or a mixture thereof, about 1.0 g/L to about 10.0 g/L HA and about 50 g/L soy peptone.

2. SMALL VOLUME VIRUS FREEZING RATE AND LYOPHILIZATION

As stated supra, the process for producing a small volume storage stable virus composition comprises (a) freezing the virus composition below its glass transition temperature ($T_g$) in a time of sixty minutes or less and (b) lyophilizing the virus composition, wherein the lyophilized virus composition is a stable for at least one year at a storage temperature of about 1° C. to about 10° C.

The $T_g$ of a virus composition is typically about −35° C. The $T_g$ of a virus composition is lower than about −35° C. (e.g., about −42° C.) in the presence of "carry over" salts such as sodium chloride. For example, sodium chloride is a component of the virus growth medium, but is not a component of the small volume formulation. Thus, certain virus formulations will contain residual quantities (i.e., a "carry over") of sodium chloride, and as such the $T_g$ may be lower than about −35° C., but is typically not lower than about −50° C.

The term "glass transition temperature" or "$T_g$" refers to the approximate midpoint of the temperature range over which the transition from a liquid to a glass state occurs. The rate at which the virus composition reaches its $T_g$ is critical for virus stability during lyophilization (e.g., see Example 2) and for long term virus storage stability (e.g., see Example 3). Stated another way, a faster freezing rate results in a more stable virus composition, thereby resulting in a smaller potency loss of the virus composition.

The term "freezing rate" refers to the rate at which the virus composition reaches its Tg. The freezing rate can be calculated as an approximate rate of temperature reduction during freezing. For example, if an initial temperature of a virus composition was 5° C. and it was frozen to its Tg of −35° C. in a time of 40 minutes, the "freezing rate" would be −1° C./minute. At similar conditions the kinetics of freezing can vary among individual containers or, in case of bulk volumes, exhibit deviations at different points. Thus, the freezing rate is an average rate of freezing observed in containers or measured at different locations of the material loaded on a tray.

The freezing rate of a small volume virus composition is about −0.5° C./minute to about −2.5° C./minute. In one embodiment, the $T_g$ is reached in a time of sixty minutes or less. In another embodiment, the $T_g$ is reached in a time of forty minutes or less. In still another embodiment, the $T_g$ is reached in a time of twenty minutes or less. The $T_g$ of a virus composition is readily determined by one of skill in the art without undue experimentation, using for example, thermodynamic measurements such as differential scanning calorimetry (DSC) (Hatley, 1992; Franks, 1992; Carpenter, 2002).

In one embodiment, a lyophilization vial comprising a small volume virus composition is pre-cooled to a temperature of about 5° C. The vial containing the pre-cooled virus composition is then placed on a lyophilization shelf and frozen to a temperature of at least −50° C., at a rate of about −1° C./minute to about −2° C./minute. In other embodiments, the vial containing pre-cooled virus composition is placed directly on a lyophilization shelf pre-frozen to a temperature of −70° C.

Lyophilization (or freeze-drying) is a dehydration technique in which the sample solution (e.g., a RSV/PIV composition) is frozen and the solvent (e.g., water or buffer) is removed by sublimation by applying high vacuum. The technique of lyophilization is well known to one of skill in the art (Rey and May, 1999).

In one embodiment, a lyophilized small volume virus composition is prepared as follows: (a) placing about 0.5 mL to 0.6 mL of the virus composition in a vial and cooling to a temperature of about 5° C.; (b) placing the vial on a lyophilization shelf and decreasing the shelf temperature from 5° C. to −50° C. at a rate of about −1.0° C. per minute to about −2.0° C. per minute; (c) holding the shelf temperature at about −50° C. for 60 minutes; (d) reducing chamber pressure to 0.10 Torr and holding the shelf temperature at about −50° C. for 30-60 minutes; (e) increasing the shelf temperature from −50° C. to 0° C. at a rate of about 1.0° C. per minute to about 2.0° C. at about 0.10 Torr and holding the shelf temperature at about 0° C. for about 540 minutes to about 720 minutes; (f) increasing the shelf temperature from 0° C. to 15° C. at a rate of about 0.5° C. per minute at about 0.10 Torr and holding the shelf temperature at about 15° C. for about 600 minutes to about 720 minutes and (g) filling the vial with nitrogen gas and hermetically sealing the vial.

In another embodiment, lyophilizing the virus composition is prepared as follows: (a) placing about 0.5 mL to 0.6 mL of the virus composition in a vial and cooling to a temperature of about 5° C.; (b) freezing a lyophilization shelf to a temperature of about −70° C.; (c) placing the vial on the lyophilization shelf and holding the temperature at about −70° C. for about 60 minutes; (d) reducing chamber pressure to 0.10 Torr and increasing the shelf temperature from −70° C. to −50° C. at a rate of about 1.0° C. per minute; (e) increasing the shelf temperature from −50° C. to 0° C. at a rate of about 1.0° C. per minute to about 2.0° C. per minute at about 0.10 Torr and holding the shelf temperature at about 0° C. for about 540 minutes to about 720 minutes; (f) increasing the shelf temperature from 0° C. to 15° C. at a rate of about 0.5° C. per minute at about 0.10 Torr and holding the shelf temperature at about 15° C. for about 600 minutes to about 720 minutes and (g) filling the vial with nitrogen gas and hermetically sealing the vial.

The lyophilized small volume virus composition (i.e., the lyophilized cake) has less than about a 1.0 log PFU loss resulting from lyophilization and less than about a 1.0 log PFU loss after one year of storage at about 1° C. to about 10° C. (e.g., see Example 2, Example 3 and Tables 2 and 4-7). In yet another embodiment, the lyophilized small volume virus composition is at least 4.0 log PFU per 0.2 mL after one year of storage at about 1° C. to about 10° C.

C. Bulk Volumes of Lyophilization Stable Virus Compositions

In another embodiment, the invention is directed to a process for producing bulk (or large) volumes of a lyophilization stable virus compositions. In one embodiment, the invention is directed to a process for producing bulk (or large) volumes of a lyophilization stable virus compositions comprising RSV, PIV, or a combination thereof. The process comprises (a) placing a liquid virus composition having a volume of at least 50 mL in a lyophilization tray (b) freezing the virus composition below its $T_g$ for at least about twenty minutes in a liquid nitrogen bath and (c) lyophilizing the virus composition. The lyophilized virus composition has less than about a 0.5 log PFU loss relative to the virus composition before the lyophilization process. The process for producing bulk volumes of the lyophilization stable virus compositions is of particular utility during the large scale production/manufacture of said virus compositions.

As defined hereinafter, a "bulk" volume or a "large" volume of a virus composition is between about 50 mL to about 2 L per lyophilization tray. In certain embodiments, a bulk volume is between about 250 mL to about 1 mL per lyophilization tray. In one particular embodiment, a bulk volume virus composition is 1 L per lyophilization tray.

1. BULK VOLUME VIRUS FORMULATION

A bulk volume virus composition is formulated with a pharmaceutically acceptable carrier which includes buffers, saline solutions, water, water for injection (WFI), protein stabilizers, sugars, amino acids, cryoprotectants, and the like.

In one embodiment, a bulk volume virus composition is formulated in a phosphate buffer solution comprising sodium and/or potassium monobasic and dibasic salts. The concentration of the phosphate buffer is about 5.0 mM to about 20 mM, with a pH range of about 6.5 to about 7.8.

In other embodiments, the 5.0 mM to about 20 mM phosphate buffer solution further comprises about 2.5 mM to about 25 mM HEPES. In certain other embodiments, the 5.0 mM to about 20 mM phosphate buffer solution further comprises about 0.1 mM to about 1 mM magnesium chloride and about 0.1 mM to about 1 mM calcium chloride.

In certain embodiments, the bulk volume virus composition is formulated in a 10 mM phosphate buffer (pH of about 6.5 to about 7.8) and further comprises about 2.5 mM to about 12.5 mM HEPES. In certain other embodiments, the 10 mM phosphate buffer solution further comprises about 0.1 mM to about 0.5 mM magnesium chloride and about 0.1 mM to about 0.5 mM calcium chloride.

In one embodiment, the 5.0 mM to about 20 mM phosphate buffer solution (pH 6.5 to 7.8, 2.5-25 mM HEPES, 0.1-1.0 mM magnesium chloride, 0.1-1.0 mM calcium chloride) further comprises sucrose, L(+)-glutamic acid, L(+)-glutamic acid monosodium salt or a mixture thereof, human albumin (HA) and/or soy peptone. In another embodiment, the 10 mM phosphate buffer solution (pH 6.5 to 7.8, 2.5-12.5 mM HEPES, 0.1-0.5 mM magnesium chloride, 0.1-0.5 mM calcium chloride) further comprises about 50 g/L sucrose, about 0.049 mM to about 2.45 mM L(+)-glutamic acid or about 0.049 mM to about 2.45 mM L(+)-glutamic acid monosodium salt or a mixture thereof, and about 1.0 g/L to about 10.0 g/L HA. In one embodiment, the about 1.0 g/L to about 10.0 g/L HA is substituted with about 50 g/L soy peptone. In yet other embodiments, the 10 mM phosphate buffer solution (pH of about 6.5 to about 7.8) comprises about 2.5 mM to about 12.5 mM HEPES, about 0.1 mM to about 0.5 mM magnesium chloride, about 0.1 mM to about 0.5 mM calcium chloride, about 50 g/L sucrose, about 0.049 mM to about 2.45 mM L(+)-glutamic acid or about 0.049 mM to about 2.45 mM L(+)-glutamic acid monosodium salt or a mixture thereof, about 1.0 g/L to about 10.0 g/L HA and about 50 g/mL soy peptone.

2. BULK VOLUME VIRUS FREEZING RATE AND LYOPHILIZATION

The method for producing a bulk volume, lyophilization stable virus composition comprises (a) placing a liquid virus composition having a volume of at least 50 mL in a lyophilization tray; (b) freezing the virus composition below its $T_g$ for at least about twenty minutes in a liquid nitrogen bath; and (c) lyophilizing the virus composition, wherein the lyophilized virus composition has less than about a 0.5 log PFU loss relative to the virus composition before lyophilization.

As described in Section B.2, the rate at which the small volume virus composition reaches its $T_g$ is critical for virus storage stability. Similarly, the rate at which the bulk volume virus composition reaches its $T_g$ is critical for virus storage stability. Thus, an important step for preparing bulk volumes of virus is freezing the virus composition below its glass transition temperature for at least about twenty minutes in a liquid nitrogen bath. Another important parameter for achieving bulk volume rapid freezing rates are the heat transfer properties, the composition and the configuration of the lyophilization tray. For example, a lyophilization tray with a large surface area further reduces the amount of time it takes for a bulk volume virus composition to reach its $T_g$. Lyophilization trays are well known in the art and include stainless steel trays, glass tray, aluminum trays, plastic trays and Lyoguard® trays. In one embodiment, the lyophilization tray is a Lyoguard® lyophilization tray. The tray is especially designed for bulk lyophilization with good heat transfer property. It consists of a micro-porous membrane designed to prevent solid particles from "flashing" out of the tray during lyophilization cycle while allowing good mass transfer of water vapor.

The $T_g$ of the virus composition is a temperature of about $-35°$ C. As stated previously, residual quantities (or "carry over") of sodium chloride from virus growth medium can further reduce the $T_g$, but not below $-50°$ C.

In certain other embodiments, lyophilizing the virus composition is further defined as (a) placing the tray comprising the frozen virus composition at a temperature of about $-50°$ C. on a lyophilization shelf pre-cooled to a temperature of about $-50°$ C. and holding the temperature for about 60 minutes; (b) reducing chamber pressure to 0.10 Torr and increasing the shelf temperature from $-50°$ C. to $-23°$ C. at a rate of about 0.23° C. per minute at about 0.10 Torr (c) holding the shelf temperature at about $-23°$ C. for about 80 hours to about 100 hours; (d) reducing chamber pressure to 0.02 Torr and increasing the shelf temperature from $-23°$ C. to 15° C. at a rate of about 0.23° C. per minute; (e) holding the shelf temperature at about 15° C. and at about 0.02 Torr for about 30 hours to about 40 hours; (f) increasing the shelf temperature from 15° C. to 25° C. at a rate of about 0.17° C. per minute at 0.02 Torr; (g) holding the shelf temperature at about 25° C. and at about 0.02 Torr for about 10 hours and (h) filling the chamber with nitrogen gas and hermetically sealing the tray under nitrogen gas in an aluminum pouch.

In other embodiments, lyophilizing the bulk volume virus composition is further defined as (a) placing the tray comprising the frozen virus composition at a temperature of about $-70°$ C. on a lyophilization shelf pre-cooled to a temperature of about $-70°$ C. and holding the temperature for about 60 minutes; (b) reducing chamber pressure to 0.10 Torr and increasing the shelf temperature from $-70°$ C. to $-23°$ C. at a rate of about 0.23° C. per minute; (c) holding the shelf temperature at about $-23°$ C. at about 0.10 Torr for about 80 to 100 hours; (d) reducing chamber pressure to 0.02 Torr and increasing the shelf temperature from $-23°$ C. to 15° C. at a rate of about 0.23° C. per minute; (e) holding the temperature at about 15° C. and 0.02 Torr for about 30 to 40 hours; (f) increasing the shelf temperature from 15° C. to 25° C. at a rate of about 0.17° C. per minute at 0.020 Torr; (g) holding the temperature at about 25° C. for about 10 hours and (h) filling the chamber with nitrogen gas and hermetically sealing the tray under nitrogen gas in an aluminum pouch.

The lyophilized bulk volume virus composition (i.e., the lyophilized cake) has less than about a 1.0 log PFU loss resulting from lyophilization, and less than about a 1.0 log PFU loss after one year of storage at about 1° C. to about 10° C. (e.g., see Example 4).

D. LIQUID VIRUS COMPOSITIONS

In another embodiment, the invention is directed to a process for producing storage stable liquid virus compositions. In one embodiment, the invention is directed to a process for producing storage stable liquid virus compositions comprising RSV, PIV, or a combination thereof. The process comprises (a) equilibrating a metal plate in a liquid nitrogen bath; (b) placing a liquid virus composition in a suitable container means; (c) inserting the container of step (b) into a metal container holder; (d) placing the metal container holder on the equilibrated metal plate of step (a) for about ten minutes; (e) removing the container from the metal container holder and (f) storing the container at a temperature from about −20° C. to about −70° C.

1. LIQUID VIRUS FREEZING AND THAWING

As set forth in step (f), the container comprising the frozen virus composition is stored at about −20° C. to about −70° C. Thawing the virus composition at room temperature brings the virus compositions back to the liquid state, wherein the thawed liquid virus composition has less than about a 0.5 log PFU loss after 6 months storage. In one embodiment, the thawed liquid virus composition is at least 4.0 log PFU/0.2 mL. In another embodiment, the thawed liquid virus composition is at least 4.0 log PFU/0.2 mL after a six month storage at a temperature of −20° C. In other embodiments, the thawed liquid virus composition is at least 4.0 log PFU/0.2 mL after a six month storage at a temperature of −70° C.

Typically, a suitable container means, with respect to a liquid virus composition, is a container which withstands temperatures in the range between about −20° C. to about −70° C. For example, a suitable container means for the production of storage stable liquid compositions is a vial, a tube, a syringe or a nasal spray device. In a certain embodiments, the container is a nasal spray device. In one embodiment, the nasal spray device is a BD Accuspray™ nasal spray device, available from BD Pharmaceutical Systems (Franklin Lakes, N.J.) or a similar nasal spray device.

The rate at which the liquid virus composition freezes is critical for virus storage stability (e.g., see Example 5). A liquid nitrogen bath is used to rapidly freeze the virus composition. The metal plate in step (a) is any metal which adequately transfers heat to the liquid nitrogen bath and away from the metal container holder of step (c). Similarly, the metal container holder in step (c) is any metal which transfers heat to the metal plate and away from the container comprising the virus. In one embodiment, the metal container holder is aluminum. In another embodiment, the metal container holder is stainless steel.

2. Liquid Virus Formulation

A liquid virus composition is formulated with a pharmaceutically acceptable carrier which includes buffers, saline solutions, water, water for injection (WFI), sugars, amino acids, cryoprotectants, and the like.

The liquid virus compositions set forth supra, are formulated in a 5.0 mM to about 20 mM phosphate buffer solution comprising sodium and/or potassium monobasic and dibasic salts and having pH of about 6.5 to about 7.8. In one embodiment, the 5.0 mM to about 20 mM phosphate buffer solution further comprises about 0.25 mM to about 25 mM HEPES. In other embodiments, the 5.0 mM to about 20 mM phosphate buffer solution further comprises about 0.01 mM to about 1 mM magnesium chloride, and about 0.01 mM to about 1 mM calcium chloride.

In certain embodiments, the liquid virus composition is formulated in a 10 mM phosphate buffer solution comprising sodium and/or potassium monobasic and dibasic salts and having a pH of about 6.5 to about 7.8. In other embodiments, the mM phosphate buffer solution further comprises about 0.25 mM to about 25 mM HEPES. In certain other embodiments, the 10 mM phosphate buffer solution further comprises about 0.01 mM to about 1 mM magnesium chloride and about 0.01 mM to about 1 mM calcium chloride.

In one embodiment, the 5.0 mM to about 20 mM phosphate buffer solution (pH of about 6.5 to about 7.8) comprising about 0.25 mM to about 25 mM HEPES, about 0.01 mM to about 1 mM magnesium chloride and about 0.01 mM to about 1 mM calcium chloride, further comprises sucrose, L(+)-glutamic acid or L(+)-glutamic acid monosodium salt or a mixture thereof, and human albumin (HA). In other embodiments, the 5.0 mM to about 20 mM phosphate buffer solution (pH of about 6.5 to about 7.8) comprising about 0.25 mM to about 25 mM HEPES, about 0.01 mM to about 1 mM magnesium chloride and about 0.01 mM to about 1 mM calcium chloride, further comprises about 75 g/L sucrose and about 4.9 mM L(+)-glutamic acid or about 4.9 mM L(+)-glutamic acid monosodium salt or a mixture thereof.

In still other embodiments, the 10 mM phosphate buffer solution (pH of about 6.5 to about 7.8) comprising about 0.25 mM to about 25 mM HEPES, about 0.01 mM to about 1 mM magnesium chloride and about 0.01 mM to about 1 mM calcium chloride, further comprises about 75 g/L sucrose and about 4.9 mM L(+)-glutamic acid or 4.9 mM L(+)-glutamic acid monosodium salt or a mixture thereof.

The liquid frozen virus composition (i.e., frozen in a spray device or vial) has less than about a 0.5 log PFU loss after "fast" freezing, and less than about a 0.5 log PFU loss after 6 months of storage at about −20° C. to about −70° C. (e.g., see Example and Tables 9-12). In yet another embodiment, the liquid frozen virus composition is at least 4.0 log PFU per 0.2 mL after 6 months of storage at about −20° C. to about −70° C.

E. Immunogenic Virus Compositions

In certain embodiments, the invention provides immunogenic compositions comprising a storage stable (frozen) liquid virus compositions comprising RSV, PIV, or a combination thereof, produced according the methods of the invention. In other embodiments, the invention provides immunogenic compositions comprising a storage stable (frozen) liquid virus compositions comprising herpes simplex virus, cytomegalovirus, Epstein-Barr virus, Varicella-Zoster virus, mumps virus, measles virus, influenza virus, poliovirus, rhinovirus, adenovirus, hepatitis A virus, hepatitis B virus, hepatitis C virus, Norwalk virus, togavirus, alphavirus, rubella virus, rabies virus, Marburg virus, Ebola virus, papilloma virus, polyoma virus, metapneumovirus, coronavirus, vesicular stomatitis virus, Venezuelan equine encephalitis virus and the like.

In certain embodiments, the frozen liquid immunogenic compositions are comprised in a nasal spray device. Typically, a storage stable (frozen) liquid virus composition of the invention is formulated and processed for administration to a mammalian subject using a liquid formulation and process of the invention (e.g., see Section D, Example 1 and Example 5), stored as a frozen liquid and thawed prior to administration to said mammalian subject.

In certain embodiments, a storage stable virus composition of the invention is a lyophilized solid (or lyophilized cake) composition. In particular embodiments, a storage stable lyophilized virus composition is dissolved, diluted or suspended in a pharmaceutically acceptable carrier and provided as an immunogenic composition suitable for administration to a mammalian subject (e.g., a human). Thus, such lyophilized compositions typically comprise the "immunogenic" composition (e.g., an attenuated RSV and/or attenuated PIV virus) and a "pharmaceutically acceptable carrier". As used hereinafter, the language "pharmaceutically acceptable carrier" is intended to include any and all solvents known in the art to be compatible with pharmaceutical administration. The use of such media and agents for pharmaceutically active substances is well known in the art. Except insofar as any conventional media or agent is incompatible with the active compound (e.g., RSV or PIV), such media are used in the compositions of the invention.

Thus, an immunogenic composition of the invention is formulated to be compatible with its intended route of administration. Examples of routes of administration include parenteral (e.g., intravenous, intradermal, subcutaneous, intramuscular, intraperitoneal), mucosal (e.g., oral, rectal, intranasal, buccal, vaginal, respiratory) and transdermal (topical). For example, a storage stable lyophilized virus immunogenic composition to be administered as an intranasal spray includes one or more of the following components: a sterile diluent such as water for injection, a saline solution, a buffers (e.g., acetates, citrates or phosphates) and agents for the adjustment of tonicity such as sodium chloride or dextrose. The pH is adjusted with acids or bases, such as hydrochloric acid or sodium hydroxide. The immunogenic composition is enclosed in a spray device, an ampoule, a disposable syringe or a single/multiple dose vial made of glass or plastic.

It is especially advantageous to formulate parenteral compositions in dosage unit form for ease of administration and uniformity of dosage. Dosage unit form as used hereinafter refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen.

All patents and publications cited herein are hereby incorporated by reference.

F. Examples

The following examples are carried out using standard techniques, which are well known and routine to those of skill in the art, except where otherwise described in detail. The following examples are presented for illustrative purpose, and should not be construed in any way as limiting the scope of this invention.

Example 1

RSV and PIV Formulation Components

The RSV and/or PIV samples described herein were formulated in one of the following phosphate buffered recipes, designated as "Formulation A1" through "Formulation E2", as follows:

Formulation A1: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose and 1.0 g/L HA. HA is Grifols® 20% (w/v) Human Albumin (Grifols USA, Los Angeles, Calif.; Catalogue No. 61953-0001-1).

Formulation A2: 10 mM phosphate buffer (pH 7.0) comprising 12.5 mM HEPES, 0.5 mM magnesium chloride, 0.5 mM calcium chloride, 2.45 mM L(+)-glutamic acid, 50 g/L sucrose and 1.0 g/L HA.

Formulation A3: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose and 1.0 g/L recombinant HA. Recombinant HA is 20% (w/v) human albumin expressed in yeast cells and sold under the trade name Recombumin® (Delta Biotechnology Ltd., Nottingham, United Kingdom)

Formulation A4: 10 mM phosphate buffer (pH 7.0) comprising 12.5 mM HEPES, 0.5 mM magnesium chloride, 0.5 mM calcium chloride, 2.45 mM L(+)-glutamic acid, 50 g/L sucrose and 1.0 g/L recombinant HA.

Formulation B1: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose and 10 g/L HA.

Formulation B2: 10 mM phosphate buffer (pH 7.0) comprising 12.5 mM HEPES, 0.5 mM magnesium chloride, 0.5 mM calcium chloride, 2.45 mM L(+)-glutamic acid, 50 g/L sucrose and 10 g/L HA.

Formulation B3: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose and 10 g/L recombinant HA.

Formulation B4: 10 mM phosphate buffer (pH 7.0) comprising 12.5 mM HEPES, 0.5 mM magnesium chloride, 0.1 mM calcium chloride, 2.45 mM L(+)-glutamic acid, 50 g/L sucrose and 10 g/L recombinant HA.

Formulation C1: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose, 50 g/L soy peptone (Hy Soy®) and 1.0 g/L HA.

Formulation C2: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose, 50 g/L soy peptone and about 1.0 g/L recombinant HA.

Formulation C3: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose, 50 g/L soy peptone and about 1.0 g/L recombinant HA.

Formulation C4: 10 mM phosphate buffer (pH 7.0) comprising 12.5 mM HEPES, 0.5 mM magnesium chloride, 0.1 mM calcium chloride, 2.45 mM L(+)-glutamic acid, 50 g/L sucrose, 50 g/L soy peptone and about 1.0 g/L HA.

Formulation D1: 10 mM phosphate buffer (pH 7.0) comprising 2.5 mM HEPES, 0.1 mM magnesium chloride, 0.1 mM calcium chloride, 0.49 mM L(+)-glutamic acid, 50 g/L sucrose and 50 g/L soy peptone.

Formulation D2: 10 mM phosphate buffer (pH 7.0) comprising 12.5 mM HEPES, 0.5 mM magnesium chloride, 0.5 mM calcium chloride, 2.45 mM L(+)-glutamic acid, 50 g/L sucrose and 50 g/L soy peptone.

Example 2

Effect of Freezing Rates on Potencies of Small Volume RSV and/or PIV Formulations During Lyophilization In this example, the freezing rates of small volume RSV and/or PIV formulations were studied to determine the optimal freezing conditions needed minimize virus potency loss.

Initially, three samples were tested containing LRSV-404, PIV3-cp45 and a combination of LRSV-404/PIV3-cp45 (Table 2). The viral bulks used in these formulations were prepared as clinical materials for Phase 1 and Phase 2 human clinical trials. Each virus sample was formulated using "Formulation A1", as set forth in Example 1. The samples were filled in 2 mL vials (0.6 mL per vial), pre-cooled to a temperature of about 5° C. and then placed on a pre-cooled (−50° C.) shelf of the lyophilizer. The glass transition temperature ($T_g$) of the virus composition (about −35° C.±5° C.) was reached in approximately forty minutes, corresponding to a freezing rate of about −1.0° C. per minute. After freezing, a lyophilization cycle was applied that included primary drying at 0° C., followed by secondary drying at 15° C.

TABLE 2

POTENCY OF SMALL VOLUME VIRUS FORMULATIONS BEFORE AND AFTER LYOPHILIZATION

| Virus | Potency (log PFU/mL) Before Lyophilization | Potency (log PFU/mL) After Lyophilization* |
|---|---|---|
| LRSV-404 | 6.5 | 6.5 |
| PIV3-cp45 | 7.7 | 7.1 |
| LRSV-404[1] | 6.5 | 6.3 |
| PIV3-cp45[1] | 7.7 | 7.5 |

(a) *= Samples where frozen at −1° C./minute
(b) LRSV-404[1]; the potency of LRSV-404[1] as determined from a combined LRSV-404/PIV-cp45 formulation.
(c) PIV-cp45[1]; the potency of PIV-cp45[1] as determined from a combined LRSV-404/PIV-cp45 formulation.

Virus potency testing was performed for initial virus bulks, the virus material in vials after the freezing step and the lyophilized samples (immediately after lyophilization). RSV was tested using the Plaque Form Unit (PFU) Assay and Vero cells (ATCC Catalogue No. CCL-18). The assay included (a) the preparation of cell monolayers in 24-well plates, (b) the preparation of 10-fold dilutions of reference and test samples, (c) infection of the cells, (d) incubation of plates for about 5 days at 32° C. and 5% $CO_2$ and (e) fixation of cells and immunostaining to visualize the plaques. PIV was tested using the Plaque Form Unit (PFU) Assay and LCC-MK2 cells that included (a) the preparation of cell monolayers in 24-well plates, (b) the preparation of 10-fold dilutions of reference and test samples, (c) infection of the cells, (d) incubation of plates for about 4 days at 32° C. and 5% $CO_2$ and (e) fixation of cells and immunostaining to visualize plaques. For both assays, the results of potency testing were considered as acceptable, if the potency of reference samples determined from the assay was within ±0.5 log PFU of the registered value.

Results of potency testing performed for RSV, PIV and RSV/PIV formulations are shown in Table 2. The data indicate minimal potency loss for formulations frozen at a rate of about −1.0° C. per minute. The results of this experiment also confirmed that RSV and PIV are compatible in a combined formulation.

RSV and/or PIV stability was further tested at faster (−2° C./minute; Table 6) and slower (−0.3° C./minutes; Table 3) freezing rates and with varying concentrations of recombinant HA (rHA), HA, soy peptone and combinations thereof. The virus samples comprised LRSV-404, LRSV-rA38, LRSV-rA42 or PIV3-cp45 liquid viral bulks prepared for Phase 1 and Phase 2 human clinical trials. Each virus sample was formulated using the formulation as indicated in the second column of Tables 3-6. The virus samples were filled in a 2 mL vial (0.5 mL per a vial), pre-cooled to a temperature of about 5° C. and then placed on a shelf of the lyophilizer. The frozen samples were lyophilized using cycles that included primary drying at 0° C. followed by secondary drying at 15° C.

Potency testing was performed for initial viral bulks, materials in vials after freezing and lyophilized samples (immediately after lyophilization). The potency testing results indicated a significant reduction of RSV or PIV potencies in samples frozen at about −0.3° C. per minute (Table 3) and a high stability of RSV or PIV in formulations frozen at faster rates of −1° C. per minute (Table 4 and Table 5) and −2° C. per minute (Table 6).

TABLE 3

POTENCY OF SMALL VOLUME RSV FORMULATIONS FROZEN AT −0.3° C./MINUTE

| Virus | Formulation[1] | Potency (log PFU/mL) Before Lyophilization | Potency (log PFU/mL) After Lyophilization | Freezing Rate |
|---|---|---|---|---|
| RSV-404 | A1 | 7.1 | 3.4 | −0.3° C./min |
| RSV-404 | A3 | 7.2 | 3.8 | −0.3° C./min |
| RSV-404 | B1 | 7.1 | 4.2 | −0.3° C./min |
| RSV-rA42 | A2 | 6.3 | 3.9 | −0.3° C./min |
| RSV-rA42 | A4 | 6.1 | 3.6 | −0.3° C./min |
| RSV-rA42 | B2 | 6.3 | 3.4 | −0.3° C./min |
| RSV-rA42 | C3 | 6.1 | 4.9 | −0.3° C./min |
| RSV-rA42 | D2 | 6.1 | 4.4 | −0.3° C./min |

Formulation[1] = Formulations A1-A4, B1, B2, C3 and D2 are described in Example 1.

TABLE 4

POTENCY OF SMALL VOLUME PIV FORMULATIONS FROZEN AT −1° C./MINUTE

| Virus | Formulation[1] | Potency (log PFU/mL) Before Lyophilization | Potency (log PFU/mL) After Lyophilization | Freezing Rate |
|---|---|---|---|---|
| PIV3-cp45 | A1 | 7.0 | 6.6 | −1° C./min |
| PIV3-cp45 | A3 | 7.0 | 6.7 | −1° C./min |
| PIV3-cp45 | B1 | 7.0 | 6.4 | −1° C./min |
| PIV3-cp45 | B3 | 7.0 | 6.6 | −1° C./min |
| PIV3-cp45 | C1 | 7.0 | 6.5 | −1° C./min |
| PIV3-cp45 | C3 | 7.0 | 6.3 | −1° C./min |
| PIV3-cp45 | D1 | 7.0 | 6.5 | −1° C./min |

Formulation[1] = Formulations A1, A3, B1, B3, C1, C3 and D1 are described in Example 1.

TABLE 5

POTENCY OF SMALL VOLUME RSV FORMULATIONS FROZEN AT −1° C./MINUTE

| Virus | Formulation[1] | Potency (log PFU/mL) Before Lyophilization | Potency (log PFU/mL) After Lyophilization | Freezing Rate |
|---|---|---|---|---|
| LRSV-404 | A1 | 6.6 | 6.3 | −1° C./min |
| LRSV-404 | C1 | 6.5 | 6.0 | −1° C./min |
| LRSV-rA42 | A2 | 5.9 | 5.8 | −1° C./min |
| LRSV-rA42 | D2 | 5.9 | 6.0 | −1° C./min |
| LRSV-rA38 | A2 | 5.7 | 5.4 | −1° C./min |
| LRSV-rA38 | B2 | 5.4 | 5.1 | −1° C./min |
| LRSV-rA38 | C4 | 5.7 | 5.3 | −1° C./min |
| LRSV-rA38 | D2 | 5.4 | 4.8 | −1° C./min |

Formulation[1] = Formulations A1, A2, B2, C1, C4 and D2 are described in Example 1.

TABLE 6

POTENCY OF SMALL VOLUME RSV AND PIV FORMULATIONS FROZEN AT −2° C./MINUTE

| Virus | Formulation[1] | Potency (log PFU/mL) Before Lyophilization | Potency (log PFU/mL) After Lyophilization | Freezing Rate |
|---|---|---|---|---|
| PIV-cp45 | B1 | 7.3 | 6.9 | −2° C./min |
| LRSV-404 | B1 | 6.3 | 6.0 | −2° C./min |
| LRSV-rA38 | B2 | 5.5 | 5.5 | −2° C./min |
| LRSV-rA38 | B4 | 5.5 | 5.3 | −2° C./min |

Formulation[1] = Formulations B1, B2 and B4 are described in Example 1.

Example 3

Storage Stability of Small Volume Formulations Comprising RSV or PIV

Storage stability of formulations described in Example 2 were evaluated by potency testing at different time points that included 3-month, 6-month, 9-month and 12-month storage at 5° C. Stability data are summarized in Table 7 below, wherein the data demonstrate minimum potency losses of the virus compositions up to one-year of storage at 5° C. The Formulation column in Table 7 represents the formulations designated in Example 1.

lyophilizer by reducing shelf temperature from 5° C. to −45° C. in 45 minutes. The lyophilization tray remained on the shelf (at −45° C.) for an additional 5 hours to allow the formulation to freeze below glass transition temperature. The actual time to reach the glass transition temperature (about −35° C.) was about 2 hours, which corresponded to a freezing rate of about −0.3° C. per minute. Subsequently, a 90 hour lyophilization cycle was applied, that included primary drying at 0° C. followed by secondary drying at 15° C. The initial formulated bulk and the lyophilized material were tested for potency by PFU Assay.

In another experiment, formulation with LRSV-rA39 was prepared using the same formulation, but the material was lyophilized using small size aluminum trays with 50-mL capacity. The material was frozen on a shelf of lyophilizer by reducing temperature from 5° C. to −40° C. in 60 minutes. The actual time to reach the glass transition temperature of the material (about −35° C.) was about 1.5 hours, which corresponded to a freezing rate of about −0.4° C. per minute. Subsequently, a 24 hour lyophilization cycle was applied that included primary drying at 0° C. followed by secondary drying at 15° C. The initial formulated bulk and the lyophilized material were tested for potency by PFU Assay.

Alternatively, two other RSV formulations were prepared using bulk lyophilization in 1-L Lyoguard® lyophilization trays. The LRSV-rA38 and LRSV-404 (grown in serum free medium) were formulated separately with 10 mM phosphate

TABLE 7

FORMULATION, FREEZING RATE AND STORAGE STABILITY DATA FOR RSV AND PIV COMPOSITIONS

| Strain | Formulation | Viral bulk | Freezing rate | *Lyo loss (log PFU) | Potency at 5° C. (log PFU/ml) | | | | | 1-year potency loss (log PFU) |
|---|---|---|---|---|---|---|---|---|---|---|
| | | | | | 0 mo | 3 mo | 6 mo | 9 mo | 12 mo | |
| LRSV-404 | A1 | S | −1° C./min | −0.3 | 6.3 | 5.9 | 5.9 | 5.9 | 5.5 | −0.8 |
| PIV3-cp45 | A1 | SF | −1° C./min | −0.4 | 6.6 | 6.3 | 5.9 | 6.0 | 5.6 | −1.0 |
| LRSV-rA42 | A2 | SF | −1° C./min | −0.1 | 5.8 | 5.4 | 5.2 | 4.9 | 4.8 | −1.0 |
| PIV3-cp45 | B1 | SF | −1° C./min | −0.6 | 6.4 | 6.2 | 6.1 | 5.9 | 5.7 | −0.7 |
| LRSV-rA38 | B2 | SF | −1° C./min | −0.3 | 5.1 | 4.8 | 4.5 | 4.2 | 4.2 | −0.9 |
| LRSV-404 | C1 | S | −1° C./min | −0.0 | 6.0 | 6.0 | 6.2 | 6.0 | 5.7 | −0.3 |
| PIV3-cp45 | C1 | SF | −1° C./min | −0.5 | 6.5 | 5.8 | 6.0 | 6.2 | 5.6 | −0.9 |
| PIV3-cp45 | C2 | SF | −1° C./min | −0.7 | 6.3 | 5.7 | 5.9 | 5.8 | 5.5 | −0.8 |
| PIV3-cp45 | D1 | SF | −1° C./min | −0.5 | 6.5 | 5.7 | 5.4 | 6.1 | 5.8 | −0.7 |
| LRSV-rA38 | D2 | SF | −1° C./min | −0.3 | 4.8 | 4.5 | 4.2 | 4.1 | 4.3 | −0.5 |

Lyo = Abbreviation for Lyophilization
mo = Abbreviation for months
S = Virus was grown in medium comprised of fetal bovine serum
SF = Virus was propagated using "serum free" growth medium Example 4

Effect of Freezing Rates on Potency of Bulk Volume RSV and/or PIV Formulations During Lyophilization To optimize the lyophilization process of large-scale production of immunogenic compositions comprising RSV, a PIV, or a combination thereof, different freezing rates for bulk (large) volume RSV or PIV formulations were tested.

The bulk RSV-404 formulation, comprising 10 mM phosphate buffer pH 7.0 (2.5 mM HEPES, 0.1 mM magnesium chloride, 0.1 mM calcium chloride, 0.49 mM L(+)-glutamic acid monosodium salt, 50 g/L sucrose and 1 g/L of HA) was prepared and lyophilized in a 1-L Lyoguard® lyophilization tray. Freezing of the material was performed on the shelf of a (pH 7.0) comprising 12.5 mM HEPES, 0.5 mM magnesium chloride, 0.5 mM calcium chloride, 2.45 mM L(+)-glutamic acid, 50 g/L sucrose and 10 g/L of HA. The virus compositions were frozen by sinking the trays into a liquid nitrogen bath for at least 20 minutes. The lyophilization trays were then placed on a pre-cooled (−50° C.) lyophilization shelf and lyophilized using a 120 hour cycle that included (a) initiation of primary drying with vacuum set to 0.10 Torr; (b) a temperature ramp (at 0.23° C./minute) to a shelf temperature of −23° C.; (c) holding the temperature at −23° C. for 80-100 hours; (d) initiation of secondary drying with vacuum set at 0.02 Torr; (e) a temperature ramp (at 0.13° C./minute) to a shelf temperature of 15° C.; (f) holding the temperature at 15° C. for 30-40 hours; (g) ramping the temperature (at 0.17° C./minute) to a shelf temperature of 25° C. and (h) holding the temperature at 25° C. for 10 hours.

Samples of formulated virus bulks and lyophilized materials were tested for potency in PFU Assay. Listed in Table 8 below are data confirming that freezing rates are critical for preservation of virus potency during lyophilization cycles. Freezing of trays on lyophilization shelves ("slow freezing") resulted in significant potency loss in lyophilized materials (Table 8, column 2) relative to freezing the trays with liquid nitrogen ("fast freezing"), in which potency loss was negligible (Table 8, column 3).

TABLE 8

EFFECT OF FREEZING RATE ON RSV POTENCY
DURING BULK LYOPHILIZATION
Potency loss after bulk lyophilization (log PFU)

| Strain | Freezing in lyophilizer | Fast freezing with liquid nitrogen |
|---|---|---|
| LRSV-404 | −1.2 | ND |
| LRSV-rA39 | −3.5 | ND |
| LRSV-404 | ND* | 0 |
| LRSV-rA38 | ND* | −0.6 |

ND* = Not determined

Example 5

Fast Freezing of Liquid RSV Formulations Filled in Nasal Spray Devices

A liquid formulation of LRSV-rA38 (grown in serum free medium) was prepared in a 10 mM phosphate buffer solution (pH 7.5) comprising 25 mM HEPES, 1.0 mM magnesium chloride, 1.0 mM calcium chloride, 75 g/L sucrose and 4.9 mM L(+)-glutamic acid. The formulation was filled into BD Accuspray™ nasal spray devices (0.23 mL per a device) and each nasal spray device was inserted into a well of an aluminum nasal spray holder (e.g., see FIG. 1) designed and manufactured by Applicant. The nasal spray holder was made from an aluminum block having 96 wells, wherein the well diameter is 0.5 mm greater than the diameter of the nasal spray device. The wells are deep enough to allow the virus sample within each nasal spray device to be below top surface of the holder (FIG. 1).

At the time of filling the nasal spray devices, a stainless steel plate (with dimensions 0.3 m×0.2 m×0.02 m) was placed into a cryocontainer filled with liquid nitrogen and the plate was equilibrated in the liquid nitrogen (i.e., until the liquid nitrogen stopped boiling). After equilibration, the volume of the liquid nitrogen in the cryocontainer was adjusted such that there was enough volume to touch the metal plate, but not touch the nasal spray holder. The nasal spray holder, containing the filled nasal spray devices, was placed on top of the "frozen" plate inside the cryocontainer and allowed to "fast freeze" for at least ten minutes. The nasal spray devices were subsequently removed from the nasal spray holder, wherein half of the nasal spray devices were stored in a freezer that was set at −70° C. and other half of the nasal spray devices were stored in a freezer that was set at −20° C.

A liquid formulation of LRSV-404 (grown in serum free medium) was also prepared in a 10 mM phosphate buffer solution (pH 7.5) comprising 2.5 mM HEPES, 0.1 mM magnesium chloride, 0.1 mM calcium chloride, 75 g/L sucrose and 4.9 mM L(+)-glutamic acid. The formulation was filled into BD Accuspray™ nasal spray devices (0.23 mL per a device), "fast" frozen and stored as described above.

Figure 2:
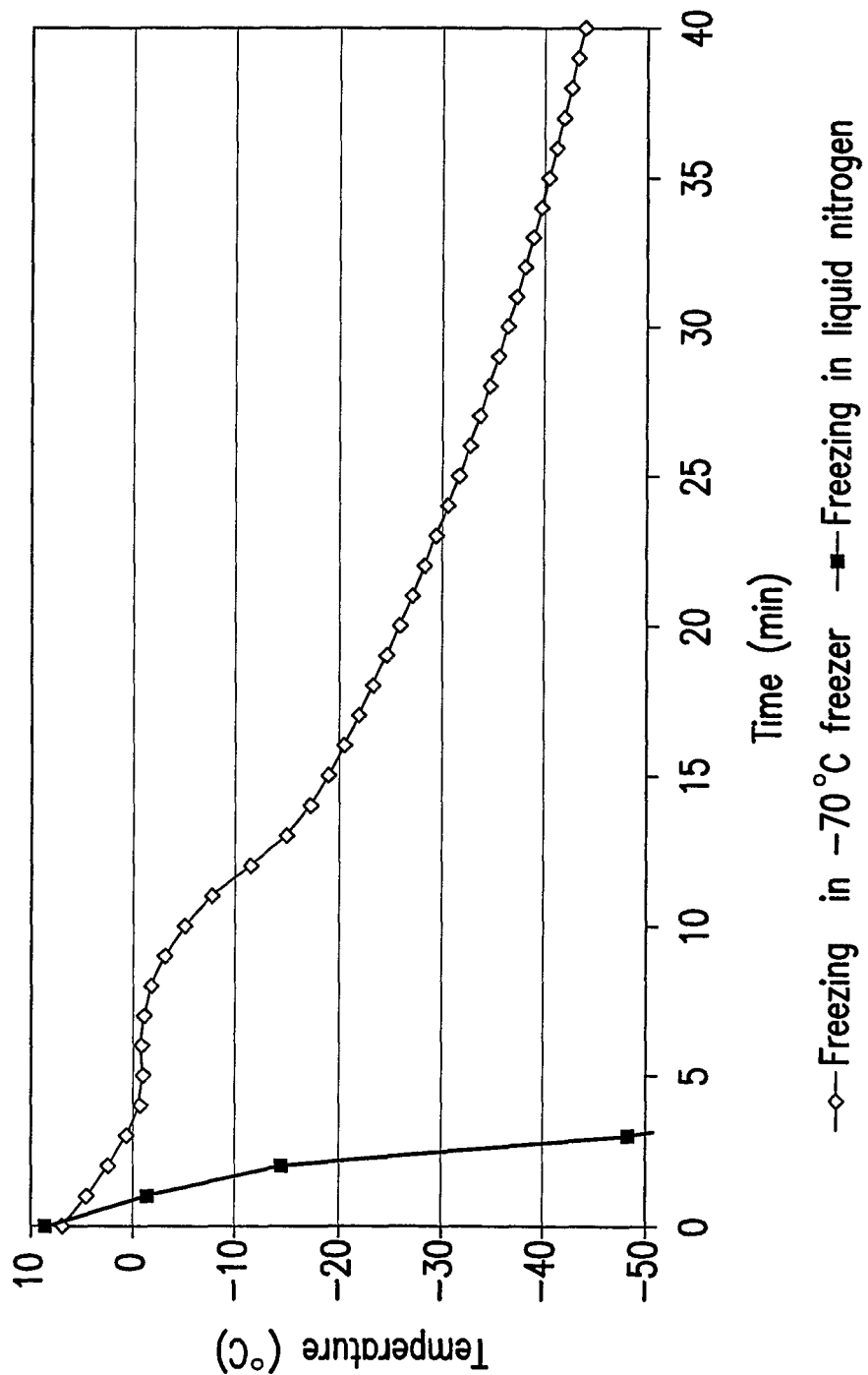
FIG. 2 shows the kinetics of freezing a formulation in a −70° C. freezer versus freezing the same formulation with liquid nitrogen. The liquid formulation was added to a BD Accuspray™ device and freezing was performed by placing the aluminum holder on a metal surface cooled by liquid nitrogen or by placing the aluminum holder on a shelf of a −70° C. freezer.

Alternatively, liquid LRSV-rA38 and liquid LRSV-404 samples were formulated and filled into the nasal spray devices as described above, but the freezing was performed by placing the nasal spray holders on a shelf of a regular freezer cooled at −70° C. and allowed to freeze for 24 hours ("slow" freezing). The data in FIG. 2 show the kinetics of "fast" freezing (FIG. 2, filled squares) and "slow" freezing (FIG. 2, open squares). Subsequently, half of the nasal spray devices were stored in a freezer that was set at −70° C. and other half of the nasal spray devices were stored in a freezer set at −20° C.

Storage stability of the samples was evaluated by potency testing at 0-month, 1-month, 3-month, 4-month and 6-month time points. The nasal spray devices (3 devices per each time point) were thawed at room temperature for about one hour. The contents of each nasal spray device was released into a tube and then tested for potency using PFU Assay.

The data presented in Tables 9-12 summarize the effect a faster freezing rate on the stability of liquid RSV formulations.

TABLE 9

THE STORAGE STABILITY (POTENCY) OF A LIQUID
LRSV-rA38 FORMULATION FROZEN AT −196° C.
AND STORED AT EITHER −20° C. OR −70° C.

| | Potency (log PFU/mL) | |
|---|---|---|
| Time (Months) | −20° C. Storage Temperature | −70° C. Storage Temperature |
| 0 | 5.6 | 5.5 |
| 1 | 5.7 | 5.5 |
| 3 | 5.6 | 5.5 |
| 4 | 5.6 | 5.6 |
| 6 | 5.6 | 5.6 |

**The potency of the liquid LRSV-rA38 formulation before freezing at −196° C. was 5.6 (log PFU/mL).

TABLE 10

THE STORAGE STABILITY (POTENCY) OF A
LIQUID LRSV-rA38 FORMULATION FROZEN AT
−70° C. AND STORED AT EITHER −20° C. OR −70° C.

| | Potency (log PFU/mL) | |
|---|---|---|
| Time (Months) | −20° C. Storage Temperature | −70° C. Storage Temperature |
| 0 | 5.1 | 5.1 |
| 1 | 4.7 | 5.1 |
| 3 | 5.0 | 5.0 |
| 4 | 5.2 | 4.6 |
| 6 | 4.8 | 5.2 |

**The potency of the liquid LRSV-rA38 formulation before freezing at −70° C. was 5.6 (log PFU/mL).

TABLE 11

THE STORAGE STABILITY (POTENCY) OF A
LIQUID LRSV-404 FORMULATION FROZEN AT
−196° C. AND STORED AT EITHER −20° C. OR −70° C.

| | Potency (log PFU/mL) | |
|---|---|---|
| Time (Months) | −20° C. Storage Temperature | −70° C. Storage Temperature |
| 0 | 5.9 | 5.9 |
| 1 | 5.8 | 5.6 |
| 3 | 6.1 | 6.1 |
| 4 | 6.0 | 5.9 |
| 6 | 5.9 | 6.0 |

**The potency of the liquid LRSV-404 formulation before freezing at −196° C. was 6.2 (log PFU/mL).

TABLE 12

THE STORAGE STABILITY (POTENCY) OF A
LIQUID LRSV-404 FORMULATION FROZEN AT −70° C.

| Time (Months) | Potency (log PFU/mL) | |
| --- | --- | --- |
| | −20° C. Storage Temperature | −70° C. Storage Temperature |
| 0 | 4.1 | 4.1 |
| 1 | 3.2 | 3.7 |
| 3 | 5.0 | 4.5 |
| 4 | 4.9 | 3.6 |
| 6 | 4.2 | 3.4 |

**The potency of the liquid LRSV-404 formulation before freezing at −70° C. was 6.2 (log PFU/mL).

It was observed from these data, that the RSV formulations frozen with the liquid nitrogen ("fast" freezing) were stable at both storage temperatures (−20° C. and −70° C.) (Table 9 and Table 11). The RSV formulations frozen on the shelf of the freezer at −70° C. ("slow" freezing) showed decreases in potencies and high variability of potency at different time points (Table 10 and Table 12).

The influence of the freezing on spray performance was evaluated by measurement of proplet Size Distribution using a Malvern SprayTec Particle Sizer. The analysis was performed for spray devices filled with the liquid LRSV-rA38 formulation described above. Droplet Size Distribution was measured for spray devices (ten devices per test) as follows: (a) nasal spray device filled with RSV, but not frozen, (b) nasal spray device filled with RSV, frozen in liquid nitrogen and stored for 3 month at −70° C., (c) nasal spray device filled with RSV, frozen in liquid nitrogen and stored for 3 month at −20° C., (d) nasal spray device filled with RSV, frozen in a −70° C. freezer and stored for 3 month at −70° C., and (e) nasal spray device filled with RSV, frozen in a −70° C. freezer and stored for 3 month at −20° C.

Since the BD Accuspray™ nasal spray device is designed to perform an intranasal vaccination by 2 consecutive sprays (separately to each nostril), each spray was analyzed. The value of fraction of droplets (%) with a particle size less than 10 μm was used as criterion (increase of mass of the fraction with the particle size less than 10 μm was unacceptable). The results of the analysis are summarized in Table 13. The freezing and 3-month storage of frozen spray devices did not affect spray performance. There was no increase observed in total mass of droplets with a diameter less than 10 μm.

TABLE 13

SPRAY PERFORMANCE OF BD ACCUSPRAY ™
DEVICES AT DIFFERENT CONDITIONS

| Freezing/ storage temperatures | Spray order | Average Dv(50) μm | Standard Deviation μm | Fraction <10 μm % | Standard Deviation % |
| --- | --- | --- | --- | --- | --- |
| Fresh fill, non-frozen | 1 | 123.2 | 15.7 | 0.3 | 0.1 |
| | 2 | 168.5 | 23.2 | 0.4 | 0.1 |
| Frozen in liquid nitrogen/stored at −70° C. | 1 | 122.3 | 15.1 | 0.2 | 0.0 |
| | 2 | 149.3 | 20.2 | 0.2 | 0.0 |
| Frozen in liquid nitrogen/stored at −20° C. | 1 | 140.7 | 27.1 | 0.2 | 0.1 |
| | 2 | 162.1 | 22.2 | 0.2 | 0.1 |
| Frozen at −70° C./ stored at −70° C. | 1 | 140.8 | 46.3 | 0.2 | 0.1 |
| | 2 | 147.3 | 19.6 | 0.2 | 0.0 |
| Frozen at −70° C./ stored at −20° C. | 1 | 136.8 | 17.9 | 0.2 | 0.1 |
| | 2 | 154.6 | 9.5 | 0.2 | 0.0 |

REFERENCES

U.S. Pat. No. 4,084,330
U.S. Pat. No. 5,489,266
U.S. Pat. No. 5,732,837
U.S. Pat. No. 5,882,651
U.S. Pat. No. 5,932,222
U.S. Pat. No. 5,993,824
U.S. Pat. No. 6,077,514
U.S. Pat. No. 6,284,254
U.S. Pat. No. 6,410,023
Ayra, *Vaccine,* 19:595-597, 2001.
Carpenter et al., "Rational design of stable lyophilized protein formulations: theory and practice". *Pharm. Biotechnol.,* 13:109-33, 2002.
Chanock et al., *Pediatrics,* 90:137-142., 1992.
Crowe, "Current Approaches to the Development of vaccines against disease Caused by Respiratory Syncytial Virus (RSV) and Parainfluenza Virus (PIV): A meeting report from the WHO Programme for Vaccine Development", *Vaccine,* 13:415-421, 1995.
Franks, "Freeze-drying: from empiricism to predictability. The significance of glass transitions". *Dev. Biol. Stand.,* 74:9-18, 1992.
Glezen et al., *Am. J. Dis. Child.* 140, 143-146, 1986.
Glezen et al., *J. Pediatr.,* 98:708-715, 1981.
Gupta et al., "Stabilization of RSV against thermal inactivation and freeze-thaw cycles for development and control of RSV vaccines and immune globulin," *Vaccine,* 14:1417-1420, 1996.
Hambling, "Survival of the RSV during storage under various conditions", *Br. J. Exp. Pathol.,* 45:647-655, 1964.
Hatley, "The effective use of differential scanning calorimetry in the optimisation of freeze-drying processes and formulations". *Dev. Biol. Stand.,* 74:105-119, 1992.
Hilleman, *Rev. Infect Dis.,* 11(Suppl. 3):S613-616, 1989.
Katz, "New vaccine development establishing priorities", Vol. 1, *Washington: National Academic Press.,* pp. 397-409, 1985.
Kneyber and Kimpen, "Current Concepts on Active Immunization Against Respiratory Syncytial Virus For Infants and Young Children", *Pediatr. Infect Dis. J.,* 21:685-696, 2002.
Lemon and Milstein, Int. J. Technol. Assess. Health Care, 10:177-184, 1994.
Martin et al., *J. Lancet,* 1035-1038, 1978.
McConnochie et al., "Variation in severity of respiratory syncytial virus infections with subtype", *J. Pediatr.* 117:52-62, 1990.
McIntosh and Chanock, *Fields Virology* (Fields and Knipe, Eds.) 1045-1075, Raven Press, Ltd., New York, 1990.
Melnick and Wallis, *Proc. Soc. Exp. Biol. Med.,* 112:894-897, 1963.
Rasmussen et al., *Am. J. Dis. Child,* 126:465-469, 1973.
Rey and May, "Freeze-Drying/Lyophilization of Pharmaceutical and Biological Products", New York: Marcel Dekker, 1999.
Robbins and Freeman, *Sci. Am.,* 259:126-133, 1988.
Stark et al., "Occurrence of respiratory syncytial virus subtypes in hospitalized children in Cleveland, Ohio from 1985 to 1988," *Pediatr. Pulmonol.,* 11:98-102, 1991.
Wertz and Sullender, *Biotech,* 20:151-176, 1992.
Wulff et al., "RSV: Properties of strains propagated in monkey kidney cell cultures", *Proc. Soc. Exp. Biol. Med.,* 115: 458-462, 1964.

What is claimed is:

1. A process for producing a storage stable virus composition, the process comprising:
    (a) freezing a virus composition comprising a respiratory syncytial virus (RSV), a parainfluenza virus (PIV), or a combination thereof below its glass transition temperature in a time of 60 minutes or less at a rate of −0.5° C. to −2.5° C. per minute; and
    (b) lyophilizing the virus, wherein the lyophilized virus composition has less than about a 17.6% log PFU loss after at least one year at a storage temperature of about 1° C. to about 10° C. as compared to the lyophilized virus composition before storage.

2. The process of claim 1, wherein the glass transition temperature is about −30° C. to about −50° C.

3. The process of claim 2, wherein the glass transition temperature of about −35° C. is reached in a time of 20 minutes or less.

4. The process of claim 1, wherein the virus composition is formulated in a 5.0 mM to about 20 mM phosphate buffer solution comprising sodium and/or potassium monobasic and dibasic salts and having a pH of about 6.5 to about 7.8.

5. The process of claim 4, further comprising about 0.25 mM to about 25 mM HEPES, about 0.01 mM to about 1 mM magnesium chloride, and about 0.01 mM to about 1 mM calcium chloride.

6. The process of claim 5, further comprising sucrose, L (+)-glutamic acid or L (+)-glutamic acid monosodium salt or a mixture of L (+)-glutamic acid/L (+)-glutamic acid monosodium salt, and human albumin (HA).

7. The process of claim 6, further comprising soy peptone.

8. The process of claim 1, wherein the virus composition has less than about a 1.0 log PFU loss after one year of storage at about 1° C. to about 10° C.

9. The process of claim 1, wherein lyophilizing the virus composition is further defined as:
    (a) placing about 0.5 mL to 0.6 mL of the virus composition in a vial and cooling to a temperature of about 5° C.;
    (b) placing the vial on a lyophilization shelf and decreasing the shelf temperature from 5° C. to −50° C. at a rate of about −1.0° C. per minute to about −2.0° C. per minute;
    (c) holding the shelf temperature at about −50° C. for 60 minutes;
    (d) reducing chamber pressure to 0.10 Torr and holding the shelf temperature at about −50° C. for 30-60 minutes;
    (e) increasing the shelf temperature from −50° C. to 0° C. at a rate of about 1.0° C. per minute to about 2.0° C. at about 0.10 Torr and holding the shelf temperature at about 0° C. for about 540 minutes to about 720 minutes;
    (f) increasing the shelf temperature from 0° C. to 15° C. at a rate of about 0.5° C. per minute at about 0.10 Torr and holding the shelf temperature at about 15° C. for about 600 minutes to about 720 minutes, and
    (g) filling the vial with nitrogen gas and hermetically sealing the vial.

10. The process of claim 1, wherein lyophilizing the virus composition is further defined as:
    (a) placing about 0.5 mL to 0.6 mL of the virus composition in a vial and cooling to a temperature of about 5° C.;
    (b) freezing a lyophilization shelf to a temperature of about −70° C.;
    (c) placing the vial on the lyophilization shelf and holding the temperature at about −70° C. for about 60 minutes;
    (d) reducing chamber pressure to 0.10 Torr and increasing the shelf temperature from −70° C. to −50° C. at a rate of about 1.0° C. per minute;
    (e) increasing the shelf temperature from −50° C. to 0° C. at a rate of about 1.0° C. per minute to about 2.0° C. per minute at about 0.10 Torr and holding the shelf temperature at about 0° C. for about 540 minutes to about 720 minutes;
    (f) increasing the shelf temperature from 0° C. to 15° C. at a rate of about 0.5° C. per minute at about 0.10 Torr and holding the shelf temperature at about 15° C. for about 600 minutes to about 720 minutes, and
    (g) filling the vial with nitrogen gas and hermetically sealing the vial.

11. A process for producing a lyophilization stable bulk volume virus composition, the process comprising:
    (a) placing a liquid virus composition having a volume of at least 50 mL in a lyophilization tray, wherein the virus composition comprises respiratory syncytial virus (RSV), a parainfluenza virus (PIV), or a combination thereof;
    (b) freezing the virus composition below its glass transition temperature for at least about 20 minutes in a liquid nitrogen bath; and
    (c) lyophilizing the virus composition,
    wherein the lyophilized virus composition has less than about a 0.5 log PFU loss relative to the virus composition before lyophilization.

12. The process of claim 11, wherein the glass transition temperature is about −35° C. to about −45° C.

13. The process of claim 11, wherein the virus composition is formulated in a 5.0 mM to about 20 mM phosphate buffer solution comprising sodium and/or potassium monobasic and dibasic salts and having a pH of about 6.5 to about 7.8.

14. The process of claim 13, further comprising about 2.5 mM to about 25 mM HEPES, about 0.1 mM to about 1 mM magnesium chloride, and about 0.1 mM to about 1 mM calcium chloride.

15. The process of claim 14, further comprising sucrose, L (+)-glutamic acid or L (+)-glutamic acid monosodium salt and human albumin (HA).

16. The process of claim 15, further comprising soy peptone.

17. The process of claim 11, wherein lyophilizing the bulk volume virus composition is further defined as:
    (a) placing the tray comprising the frozen virus composition at a temperature of about −50° C. on a lyophilization shelf pre-cooled to a temperature of about −50° C. and holding the temperature for about 60 minutes;
    (b) reducing chamber pressure to 0.10 Torr and increasing the shelf temperature from −50° C. to −23° C. at a rate of about 0.23° C. per minute at about 0.10 Torr;
    (c) holding the shelf temperature at about −23° C. for about 80 hours to about 100 hours;
    (d) reducing chamber pressure to 0.02 Torr and increasing the shelf temperature from −23° C. to 15° C. at a rate of about 0.23° C. per minute;
    (e) holding the shelf temperature at about 15° C. and at about 0.02 Torr for about 30 hours to about 40 hours;
    (f) increasing the shelf temperature from 15° C. to 25° C. at a rate of about 0.17° C. per minute at 0.02 Torr;
    (g) holding the shelf temperature at about 25° C. and at about 0.02 Torr for about 10 hours, and
    (h) filling the chamber with nitrogen gas and hermetically sealing the tray under nitrogen gas in an aluminum pouch.

18. The process of claim 11, wherein lyophilizing the bulk volume virus composition is further defined as:
    (a) placing the tray comprising the frozen virus composition at a temperature of about −70° C. on a lyophilization shelf pre-cooled to a temperature of about −70° C. and holding the temperature for about 60 minutes;

(b) reducing chamber pressure to 0.10 Torr and increasing the shelf temperature from −70° C. to −23° C. at a rate of about 0.23° C. per minute;

(c) holding the shelf temperature at about −23° C. at about 0.10 Torr for about 80 to 100 hours;

(d) reducing chamber pressure to 0.02 Torr and increasing the shelf temperature from −23° C. to 15° C. at a rate of about 0.23° C. per minute;

(e) holding the temperature at about 15° C. and 0.02 Torr for about 30 to 40 hours;

(f) increasing the shelf temperature from 15° C. to 25° C. at a rate of about 0.17° C. per minute at 0.02 Torr;

(g) holding the temperature at about 25° C. for about 10 hours, and (h) filling the chamber with nitrogen gas and hermetically sealing the tray under nitrogen gas in an aluminum pouch.

* * * * *

UNITED STATES PATENT AND TRADEMARK OFFICE
CERTIFICATE OF CORRECTION

| | | |
|---|---|---|
| PATENT NO. | : 8,603,796 B2 | Page 1 of 1 |
| APPLICATION NO. | : 10/582461 | |
| DATED | : December 10, 2013 | |
| INVENTOR(S) | : Look et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2182 days.

Signed and Sealed this
Twenty-first Day of July, 2015

Michelle K. Lee
*Director of the United States Patent and Trademark Office*